United States Patent [19]
Scirica et al.

[11] Patent Number: 5,908,428
[45] Date of Patent: Jun. 1, 1999

[54] STITCHING DEVICES FOR HEART VALVE REPLACEMENT SURGERY

[75] Inventors: Paul A. Scirica, Huntington, Conn.; Stephen W. Zlock, Hawthorne, N.Y.

[73] Assignee: United States Surgical Corporation, Norwalk, Conn.

[21] Appl. No.: 08/932,569

[22] Filed: Sep. 19, 1997

Related U.S. Application Data

[60] Provisional application No. 60/047,767, May 27, 1997.

[51] Int. Cl.$^6$ ........................................... A61B 17/04
[52] U.S. Cl. .......................... 606/139; 606/145; 606/148; 206/63.3; 206/339; 221/113; 221/119; 221/191; 222/144
[58] Field of Search ................................ 606/147–148; 206/63.3, 339, 340; 221/113, 119, 191; 222/144

[56] References Cited

U.S. PATENT DOCUMENTS

| | | |
|---|---|---|
| 984,756 | 2/1911 | Frisch . |
| 1,037,864 | 9/1912 | Saxton . |
| 1,131,163 | 3/1915 | Steedman . |
| 1,155,378 | 10/1915 | Steedman . |
| 1,293,565 | 2/1919 | Smit . |
| 1,293,660 | 2/1919 | Armstrong . |
| 1,449,087 | 3/1923 | Bugbee . |
| 1,876,792 | 9/1932 | Thompson . |
| 2,213,830 | 9/1940 | Anastasi . |
| 2,601,564 | 6/1952 | Smith . |
| 2,716,615 | 8/1955 | Voris et al. . |
| 2,880,728 | 4/1959 | Rights . |
| 3,073,311 | 1/1963 | Tibbs et al. . |
| 3,090,386 | 5/1963 | Curtis . |
| 3,349,772 | 10/1967 | Rygg . |
| 3,470,875 | 10/1969 | Johnson . |
| 3,664,345 | 5/1972 | Dabbs et al. . |
| 3,714,671 | 2/1973 | Edwards et al. . |

(List continued on next page.)

FOREIGN PATENT DOCUMENTS

| | | |
|---|---|---|
| 0482881 | 4/1992 | European Pat. Off. . |
| 0535906 | 4/1993 | European Pat. Off. . |
| 0541987 | 5/1993 | European Pat. Off. . |
| 0601676 | 6/1994 | European Pat. Off. . |
| 0647431 | 4/1995 | European Pat. Off. . |
| 337579 | 12/1903 | France . |
| 1251905 | 10/1967 | Germany . |
| 9109097 | 10/1991 | Germany . |
| 4124383 | 5/1992 | Germany . |
| 4124381 | 8/1992 | Germany . |
| 4127812 | 2/1993 | Germany . |
| 4139628 | 3/1993 | Germany . |
| 1103-854 | 7/1984 | U.S.S.R. . |
| 1505-514 | 9/1989 | U.S.S.R. . |
| 1725847 | 4/1992 | U.S.S.R. . |
| 586661 | 3/1947 | United Kingdom . |
| 914298 | 1/1963 | United Kingdom . |
| 1249853 | 10/1971 | United Kingdom . |
| 2260704 | 9/1991 | United Kingdom . |
| WO 93/01750 | 2/1993 | WIPO . |

OTHER PUBLICATIONS

"Design in Action", Machine Design, vol. 903, (Feb. 28, 1963).

"VIII. Näh–Instrumente und Nähmaterial", Aesculap Catalog, p. 401, (1905).

*Primary Examiner*—Gary Jackson

[57] ABSTRACT

There are provided surgical suturing apparatus or stitching devices particularly suited for use in suturing artificial heart valves to heart tissue during heart valve replacement surgery. The disclosed apparatus include a stationary jaw oriented at a predetermined angle relative to the apparatus to facilitate suturing through the artificial valve in a direction generally parallel to the axis of the valve. One embodiment of the stitching device utilizes a pair of surgical needles or incision members joined by a single length of suture material. There are also disclosed disposable loading units for providing suture - needle assemblies to the suturing apparatus. Also disclosed are methods of suturing an artificial heart valve to heart tissue using the disclosed apparatus.

19 Claims, 29 Drawing Sheets

U.S. PATENT DOCUMENTS

| | | |
|---|---|---|
| 3,807,407 | 4/1974 | Schweitzer . |
| 3,842,840 | 10/1974 | Schweitzer . |
| 3,901,244 | 8/1975 | Schweitzer . |
| 3,946,740 | 3/1976 | Bassett . |
| 4,021,896 | 5/1977 | Stierlein . |
| 4,034,850 | 7/1977 | Mandel et al. . |
| 4,038,988 | 8/1977 | Perisse . |
| 4,109,658 | 8/1978 | Hughes . |
| 4,161,951 | 7/1979 | Scanlan, Jr. . |
| 4,164,225 | 8/1979 | Johnson et al. . |
| 4,182,341 | 1/1980 | Perri . |
| 4,236,470 | 12/1980 | Stenson . |
| 4,266,552 | 5/1981 | Dutcher et al. . |
| 4,345,601 | 8/1982 | Fukuda . |
| 4,373,530 | 2/1983 | Kilejian . |
| 4,471,781 | 9/1984 | DiGiovanni et al. . |
| 4,491,135 | 1/1985 | Klein . |
| 4,549,545 | 10/1985 | Levy . |
| 4,580,567 | 4/1986 | Schweitzer et al. . |
| 4,621,640 | 11/1986 | Mulhollan et al. . |
| 4,635,638 | 1/1987 | Weintraub et al. . |
| 4,823,794 | 4/1989 | Pierce . |
| 4,826,487 | 5/1989 | Winter . |
| 4,827,931 | 5/1989 | Longmore . |
| 4,834,713 | 5/1989 | Suthanthiran . |
| 4,890,615 | 1/1990 | Caspari et al. . |
| 4,898,155 | 2/1990 | Ovil et al. . |
| 4,917,089 | 4/1990 | Sideris . |
| 4,923,461 | 5/1990 | Caspari et al. . |
| 4,935,027 | 6/1990 | Yoon . |
| 4,957,498 | 9/1990 | Capspari et al. . |
| 4,983,176 | 1/1991 | Cushman et al. . |
| 5,059,201 | 10/1991 | Asnis . |
| 5,100,042 | 3/1992 | Christoudias . |
| 5,123,528 | 6/1992 | Brown et al. . |
| 5,171,257 | 12/1992 | Ferzli . |
| 5,181,919 | 1/1993 | Bergman et al. . |
| 5,188,636 | 2/1993 | Fedotov . |
| 5,207,693 | 5/1993 | Phillips . |
| 5,217,471 | 6/1993 | Burkhart . |
| 5,219,359 | 6/1993 | McQuilkin et al. . |
| 5,224,948 | 7/1993 | Abe et al. . |
| 5,242,458 | 9/1993 | Bendel et al. . |
| 5,254,126 | 10/1993 | Filipi et al. . |
| 5,259,846 | 11/1993 | Granger et al. . |
| 5,261,917 | 11/1993 | Hasson et al. . |
| 5,281,220 | 1/1994 | Blake, III . |
| 5,284,488 | 2/1994 | Sideris . |
| 5,300,082 | 4/1994 | Sharpe et al. . |
| 5,306,290 | 4/1994 | Martins et al. . |
| 5,336,191 | 8/1994 | Davis et al. . |
| 5,344,061 | 9/1994 | Crainich . |
| 5,366,480 | 11/1994 | Corriveau et al. . |
| 5,389,103 | 2/1995 | Melzer et al. . |
| 5,433,727 | 7/1995 | Sideris . |
| 5,454,823 | 10/1995 | Richardson et al. . |
| 5,474,057 | 12/1995 | Makower et al. . |
| 5,478,344 | 12/1995 | Stone et al. . |
| 5,478,345 | 12/1995 | Stone et al. . |
| 5,480,406 | 1/1996 | Nolan . |
| 5,571,090 | 11/1996 | Sherts . |
| 5,618,270 | 4/1997 | Orejola . |
| 5,632,751 | 5/1997 | Piraka . |
| 5,632,752 | 5/1997 | Buelna . |
| 5,645,552 | 7/1997 | Sherts . |

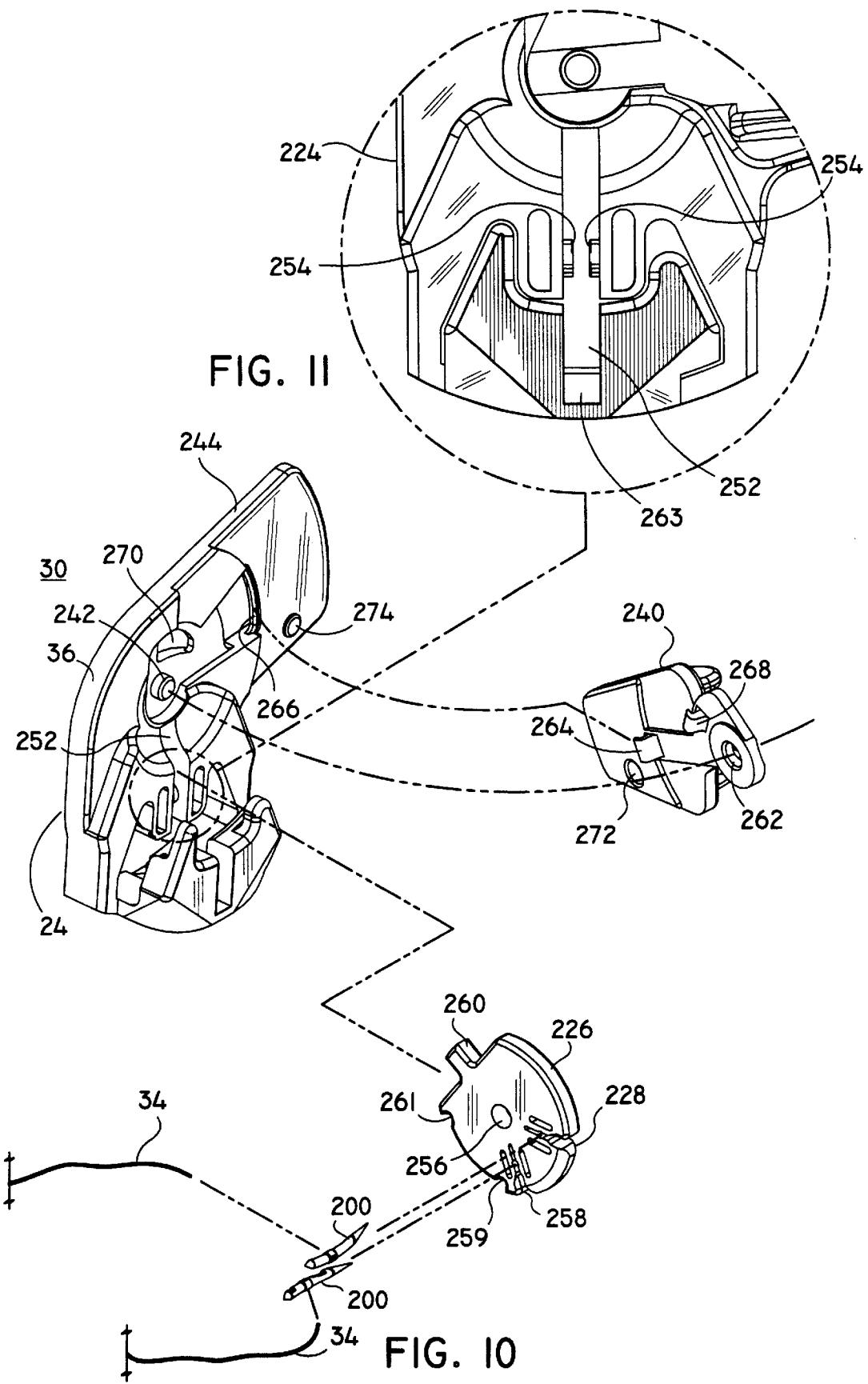

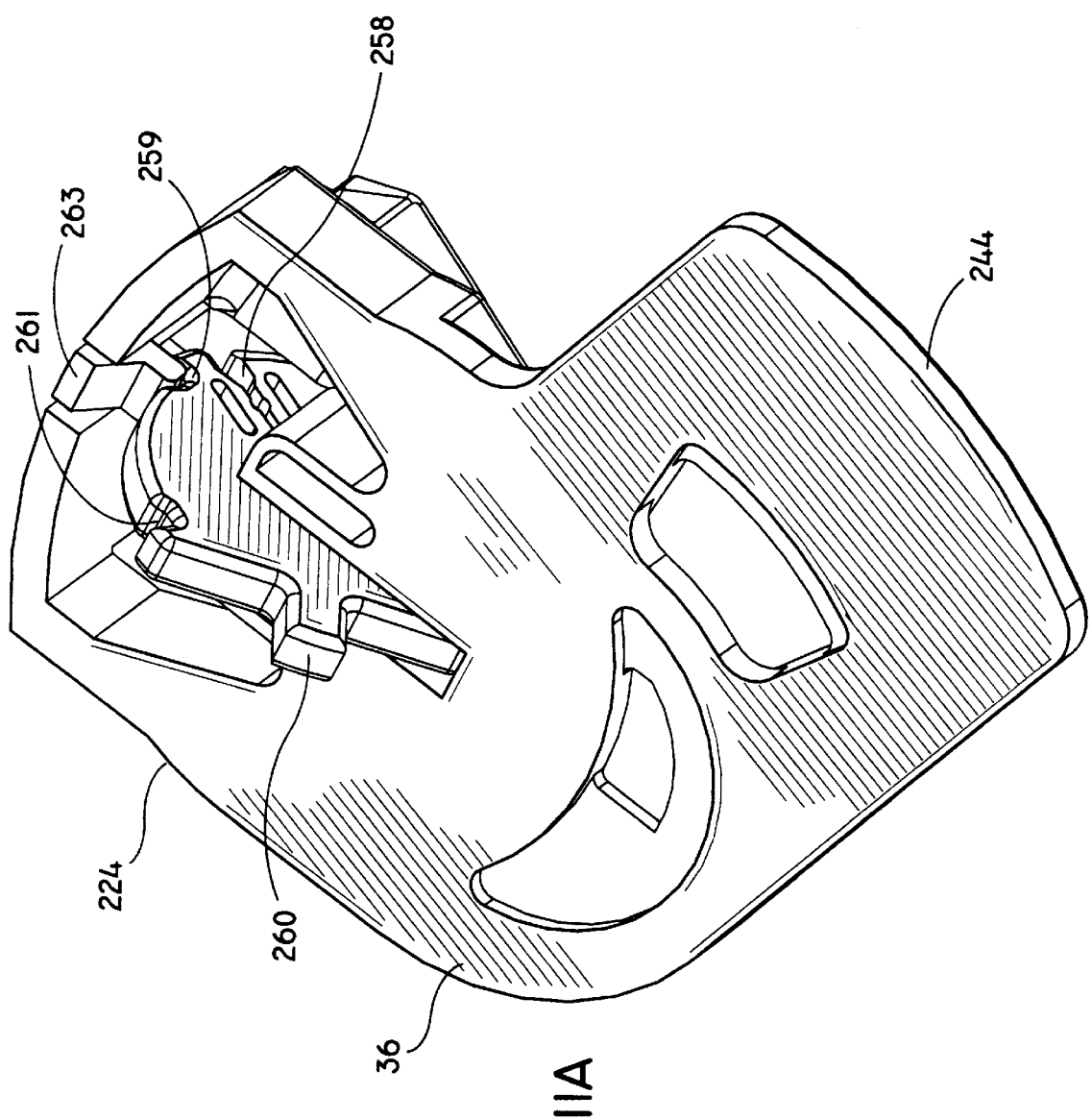

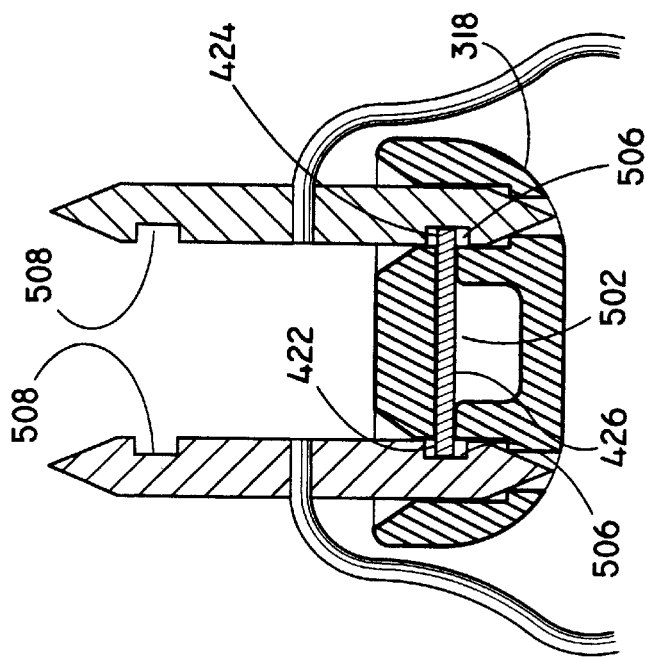
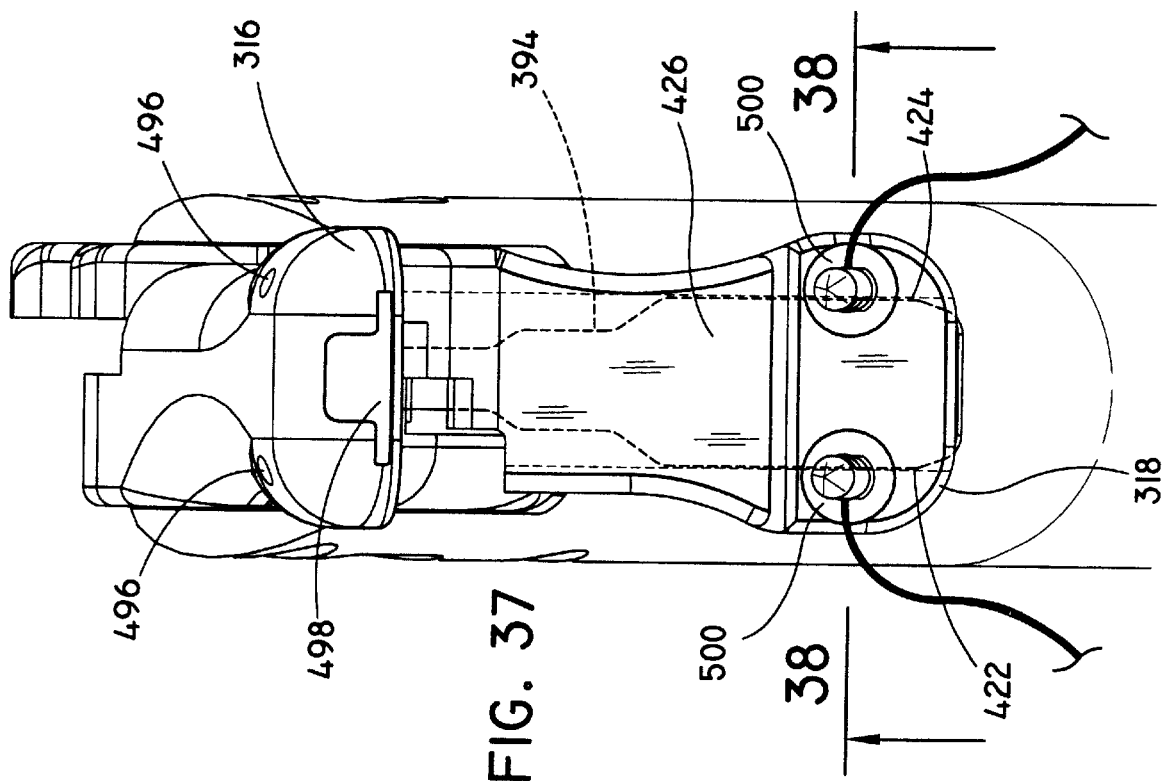
FIG. 38
FIG. 37

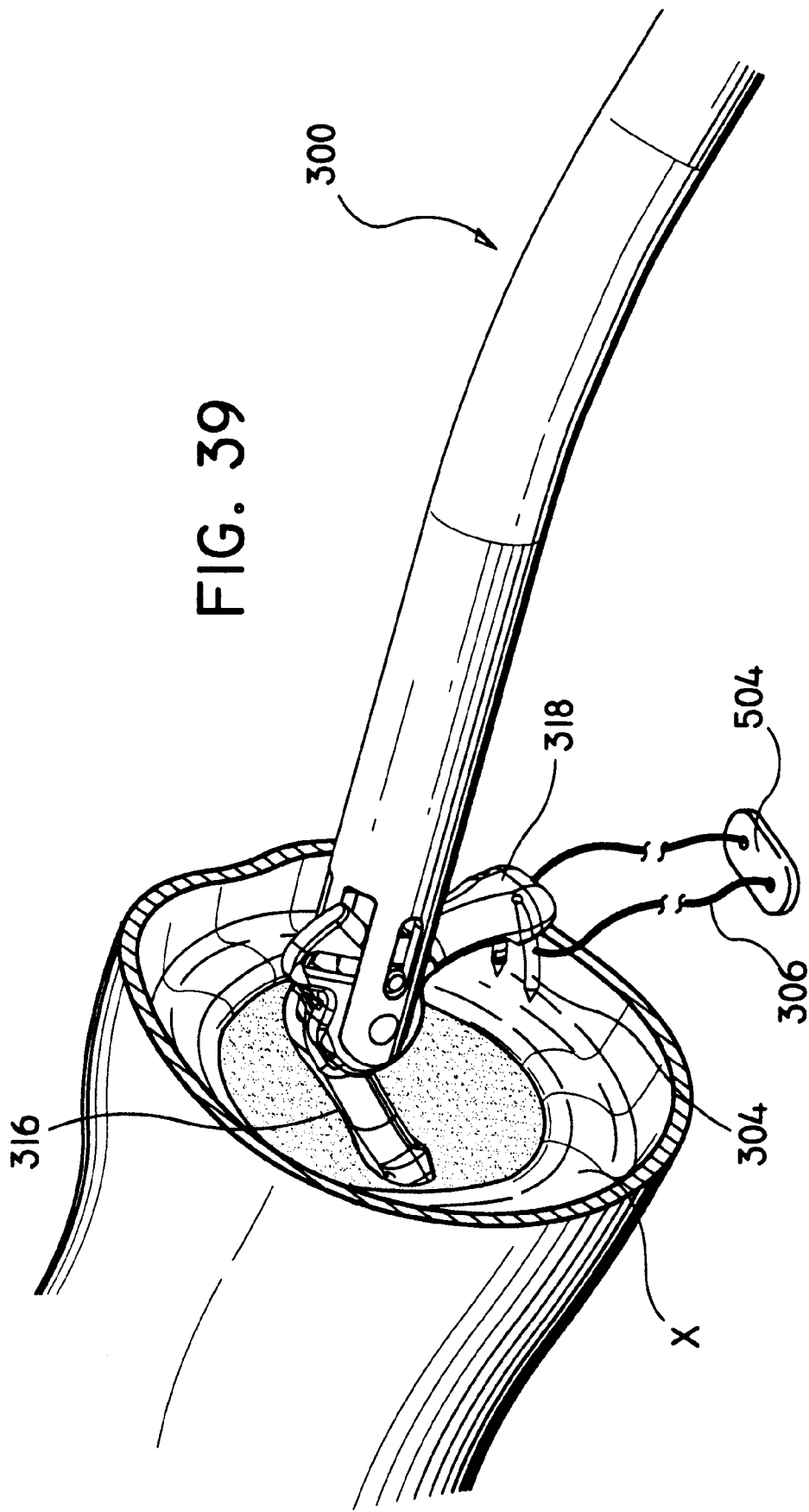

STITCHING DEVICES FOR HEART VALVE REPLACEMENT SURGERY

CROSS REFERENCE TO RELATED APPLICATION

This disclosure claims priority to Provisional U.S. patent application Ser. No. 60/047,767, filed May 27, 1997, and entitled "SURGICAL SUTURING APPARATUS WITH ANGLED JAWS AND DISPOSABLE LOADING UNIT".

BACKGROUND

1. Technical Field

The technical field relates generally to surgical suturing instrumentation and, more particularly, to surgical suturing apparatus having angled jaw structure for use in heart valve replacement surgery and to disposable loading units containing surgical needles for use with the surgical suturing apparatus.

2. Background of Related Art

The diagnosis and treatment of coronary disease and related conditions often requires repair or replacement of the valves located within the heart. Various factors, such as, for example, calcification, may result in the mitrial or aortic valves becoming impaired or functionally inoperative requiring replacement. Where replacement of a heart valve is indicated, in general, the dysfunctional valve is cut out and replaced with either an artificial, synthetic heart valve or a harvested porcine heart valve. The replacement valve is typically sutured in place of the original valve.

It is common to access the heart in a patient's thoracic cavity by making a longitudinal incision in the chest. This procedure, referred to as a median sternotomy includes cutting through the sternum and forcing the two opposing halves of the rib cage to be spread apart allowing access to the thoracic cavity and thus the heart.

Once access to the thoracic cavity has been achieved, surgery on the heart to effect valve replacement may be performed. During some procedures, the heart beat is arrested by infusion of a cardioplegic fluid, such as potassium chloride (kcl), to paralyze the myocardium while blood flow circulation is maintained through known heart bypass techniques. Alternatively, the heart is allowed to beat to maintain circulation, while a localized area of the heart, on which surgery is to be performed, is locally immobilized.

The heart is incised and the defective valve is cut away leaving a surrounding area of locally tougher tissue. Known heart valve replacement techniques typically include individually passing individual sutures through the tough tissue to form an array of sutures. Free ends of the sutures are extended out of the thoracic cavity and laid, spaced apart, on the patient's body. The free ends of the sutures are then individually threaded through an edge around the circumference of the replacement valve or a supporting cuff. Once all sutures have been run through the valve, all the sutures are pulled up taut and the valve is slid or "parachuted" down into place adjacent the tough tissue. Thereafter, the replacement valve is secured in place using the sutures.

While the above described procedures are sufficient to successfully install sutures within heart valve tissue, and position an artificial heart valve within the heart and subsequently suture the valve to the tissue, they are particularly time consuming. Therefore, a need exists for apparatus and procedures of quickly and efficiently suturing artificial heart valves within the heart.

SUMMARY

There is disclosed a first embodiment of a stitching device or surgical suturing instrument for use in heart valve replacement surgery which generally includes a housing and an elongated body portion extending distally from the housing. A first or stationary jaw is mounted on a distal end of the body portion and is oriented at a predetermined angle relative to a longitudinal axis of the body portion, the predetermined angle being greater than 0° relative to the longitudinal axis of the body portion. A second or movable jaw is also mounted on the distal end of the elongated body portion and is movable between a first position adjacent the stationary jaw and a second position spaced apart from the stationary jaw. The first jaw may also be movable relative to the body portion. At least one handle is provided and is pivotally mounted to the housing, the movable jaw being movable in response to actuation of the handle. A securing mechanism for alternately engaging and releasing a surgical needle within at least one of the stationary and movable jaws is also provided.

There is also disclosed a first embodiment of a disposable loading unit for use with the surgical suturing apparatus. The loading unit has a base and apparatus receiving structure movably mounted on the base. The apparatus receiving structure is configured to receive a distal end of the surgical suturing apparatus. A needle supply station having a needle support member is movably mounted on the base, the needle support member being configured to releasably hold at least one surgical needle thereon. Preferably, the apparatus receiving structure is pivotally mounted on the base. The needle support member is preferably rotatably mounted on the base. The needle support member is movable between a first position presenting a first surgical needle to the distal end of the surgical suturing apparatus and a second position presenting a second surgical needle to the distal end of the surgical suturing apparatus.

In a preferred embodiment of the disposable loading unit, the apparatus receiving structure is movable within a first plane, and the needle support member is movable within a second plane substantially perpendicular to the first plane.

There is also disclosed a second preferred embodiment of a surgical suturing apparatus or a dual needle stitching device for use in heart valve replacement surgery which generally includes a housing, a body portion extending distally from the housing and a first or stationary jaw mounted to a distal end of the housing, the stationary jaw configured to receive a pair of surgical needles or surgical incision members within recesses therein.

The dual needle stitching device also includes a second or movable jaw mounted to the distal end of the housing, the movable jaw also configured to receive the pair of surgical needles or surgical incision members within recesses therein. The first jaw may also be movable relative to the body portion. At least one handle is movably mounted on the housing, the movable jaw movable relative to the stationary jaw in response to actuation of the at least one handle. A securing mechanism operatively associated with the movable jaw and the stationary jaw is also provided. The securing mechanism is operable to alternately secure the pair of surgical incision members within the stationary jaw and the movable jaw.

There is also disclosed an alternate embodiment of a disposable loading unit for use with the dual needle stitching device having a needle support with a plurality of needle supply stations thereon, each needle supply station configured to releasably retain a pair of surgical needles connected by a single length of suture material. A suture support is affixed to the needle support, the suture support having at least one tube for receipt of the length of suture material.

Each needle station of the plurality of needle stations has a center stud and first and second flexible arms adjacent the center stud, a first needle of the pair of needles is retained between the first flexible arm and the stud and a second needle of the pair of needles is retained between the second flexible arm and the stud.

There is also disclosed a method of suturing an artificial heart valve to heart tissue by providing a suturing device having a first jaw and a second jaw, and a pair of needles, connected by a single length of suture material, releasably retained within one of the first and second jaws. The jaws are then positioned adjacent the heart tissue and the jaws are closed to pierce the heart tissue with the pair of needles. The pair of needles are then released from the one of the first and second jaws and grasped within the other of the first and second jaws. The first and second jaws are the opened to draw the length of suture material through the tissue until a pledget on the suture material is drawn adjacent the tissue. Preferably, a pledget on the suture is drawn up against the heart tissue. The needles are then disconnected from the suture and a subsequent needle or suture passer is used to thread the sutures through the cuff on the artificial heart valve. Once all the sutures have been passed through the cuff, the heart valve assembly is moved or "parachuted" down the sutures and into place within the heart tissue and the sutures are tied off.

BRIEF DESCRIPTION OF THE DRAWINGS

Various embodiments are described herein with reference to the drawings, wherein:

FIG. 4A is a cross-sectional view taken along line 4A—4A of FIG. 4;

FIG. 4B is a sectional view taken along line 4B—4B of FIG. 4A;

FIG. 4C is a sectional view taken along line 4C—4C of FIG. 4A;

FIG. 10 is a perspective view, with parts separated, of the loading unit of FIG. 8;

FIG. 11 is an enlarged area of detail view of FIG. 10;

FIG. 11A is a perspective view of the underside of the loading unit of FIG. 8;

FIG. 37 is an end view taken along line 37—37 of FIG. 36;

FIG. 38 is a sectional view taken along line 38—38 of FIG. 37 and illustrating the needle being retained within a jaw by a blade associated with the jaw;

FIG. 39 is a perspective view of the distal end portion of the stitching device of FIG. 26 with the double needle and suture installed thereon and in position to suture a heart valve cuff associated with a replacement heart valve to heart tissue;

DESCRIPTION OF THE PREFERRED EMBODIMENTS

Figure 1:
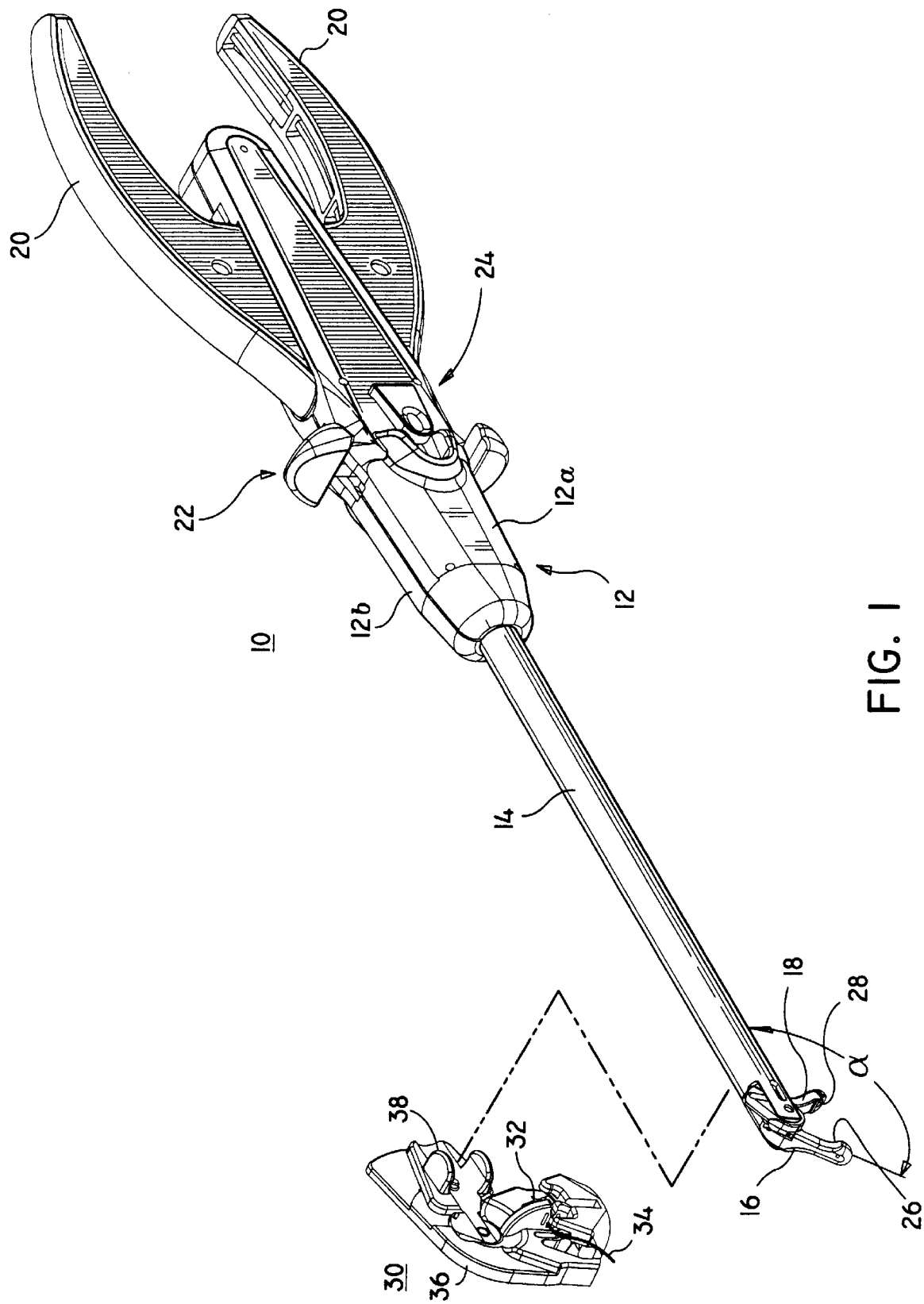
FIG. 1 is a perspective view of a surgical suturing apparatus having angled jaw structure and a disposable loading unit for installing a surgical needle into the angled jaw structure.

Referring to FIG. 1, there is illustrated a preferred embodiment of a surgical suturing apparatus 10 which is particularly suited for positioning and passing a surgical needle through dense tissue structures and prosthetics in limited access areas, such as, for example, in suturing replacement heart valves during heart valve surgery. While the following description of apparatus 10 is given with regard to its use in heart valve replacement surgery, it is specifically contemplated that apparatus 10 will find use in other surgical procedures. Surgical suturing apparatus 10 generally includes a handle housing 12 having housing halves 12a and 12b at a proximal end and an elongated tubular housing or body portion 14 extending distally from handle 12. As used herein, the term "proximal" refers to that portion of the apparatus, or component thereof, closer to the user while the term "distal" refers to that portion of the apparatus, or component thereof, further from the user.

A pair of needle receiving jaws including a first stationary jaw 16 and a second or movable jaw 18 are mounted on a distal end of body portion 14. First or stationary jaw 16 may also be movable as described below. Stationary jaw 16 is mounted at a predetermined angle α relative to a longitudinal axis of body portion 14 to facilitate access when used in heart valve surgery. The angle a is greater than 0° and obviously not 180°. Preferably, stationary jaw 16 is mounted at an angle of between approximately 60 degrees relative to body portion 14. A pair of handles 20 are provided on handle housing 12 and control the movement of movable jaw 18 with respect to stationary jaw 16. Preferably, movable jaw 18 moves through an arc of approximately 50 degrees relative to stationary jaw 16. It should be appreciated that alternatively, both jaws could be movable.

Surgical suturing apparatus 10 further includes a securing mechanism 22 which is provided to releasably and alternately secure a surgical needle within stationary jaw 16 and movable jaw 18. A loading mechanism 24 is provided to override securing mechanism 22 and enable a surgical needle to be loaded in one or both of the jaws. In order to receive the surgical needle therein, stationary jaw 16 includes a needle receiving recess 26 and movable jaw 18 includes a needle receiving recess 28.

A novel disposable loading unit 30 is provided to supply one or more surgical needles 32 having a length of suture material 34 attached thereto to surgical suturing apparatus 10. Disposable loading unit 30 generally includes a body portion 36 and apparatus receiving structure 38 movably mounted on body portion 36. Apparatus receiving structure 38 is configured to receive body portion 14 of surgical suturing apparatus 10 and position jaws 16 and 18 about surgical needle 32 in a position such that surgical needle 32 can be precisely and positively positioned within recesses 26 and 28 of jaws 16 and 18, respectively.

Figure 2:
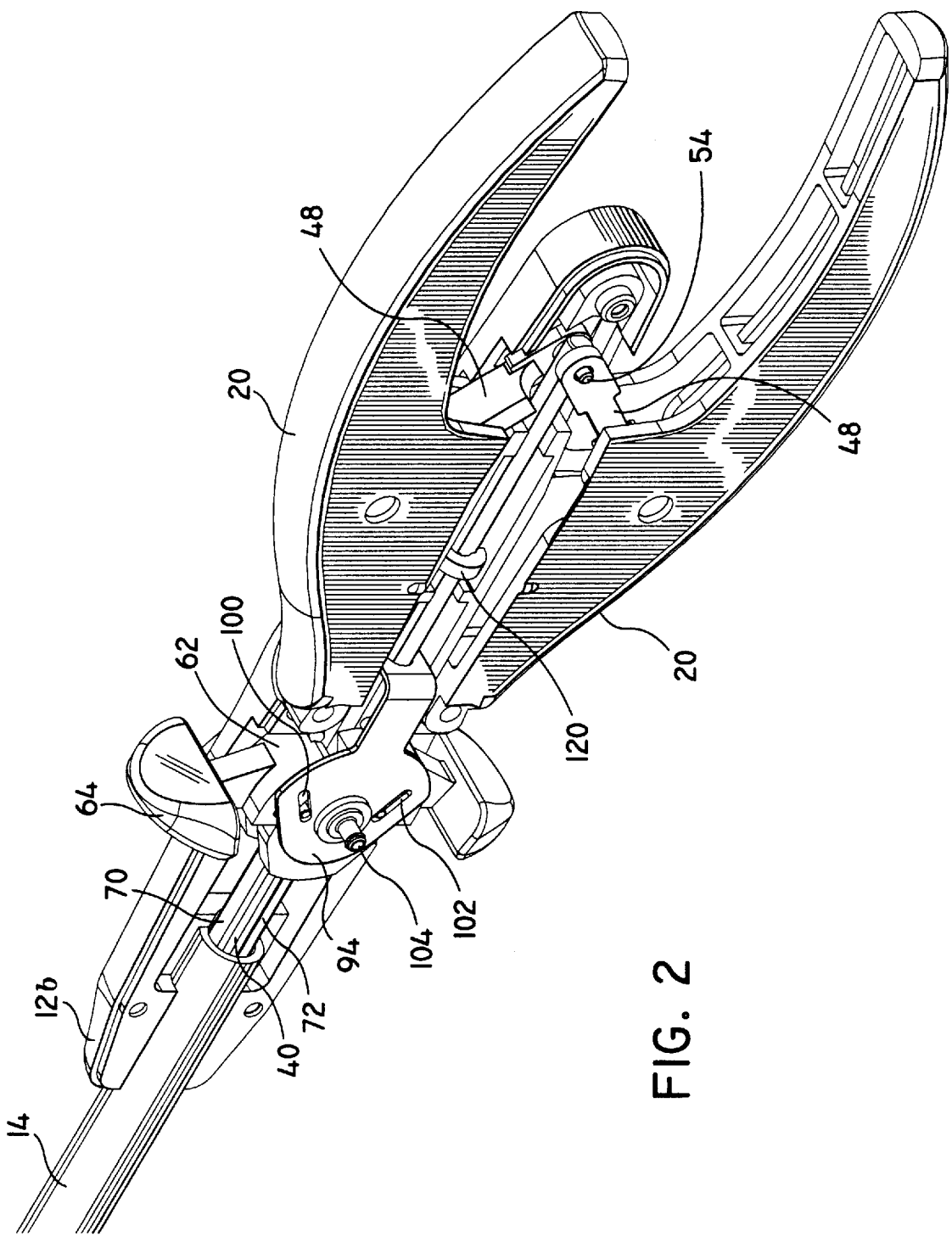
FIG. 2 is a perspective view of the handle portion of the surgical suturing apparatus of FIG. 1 with a housing half removed.
Figure 3:
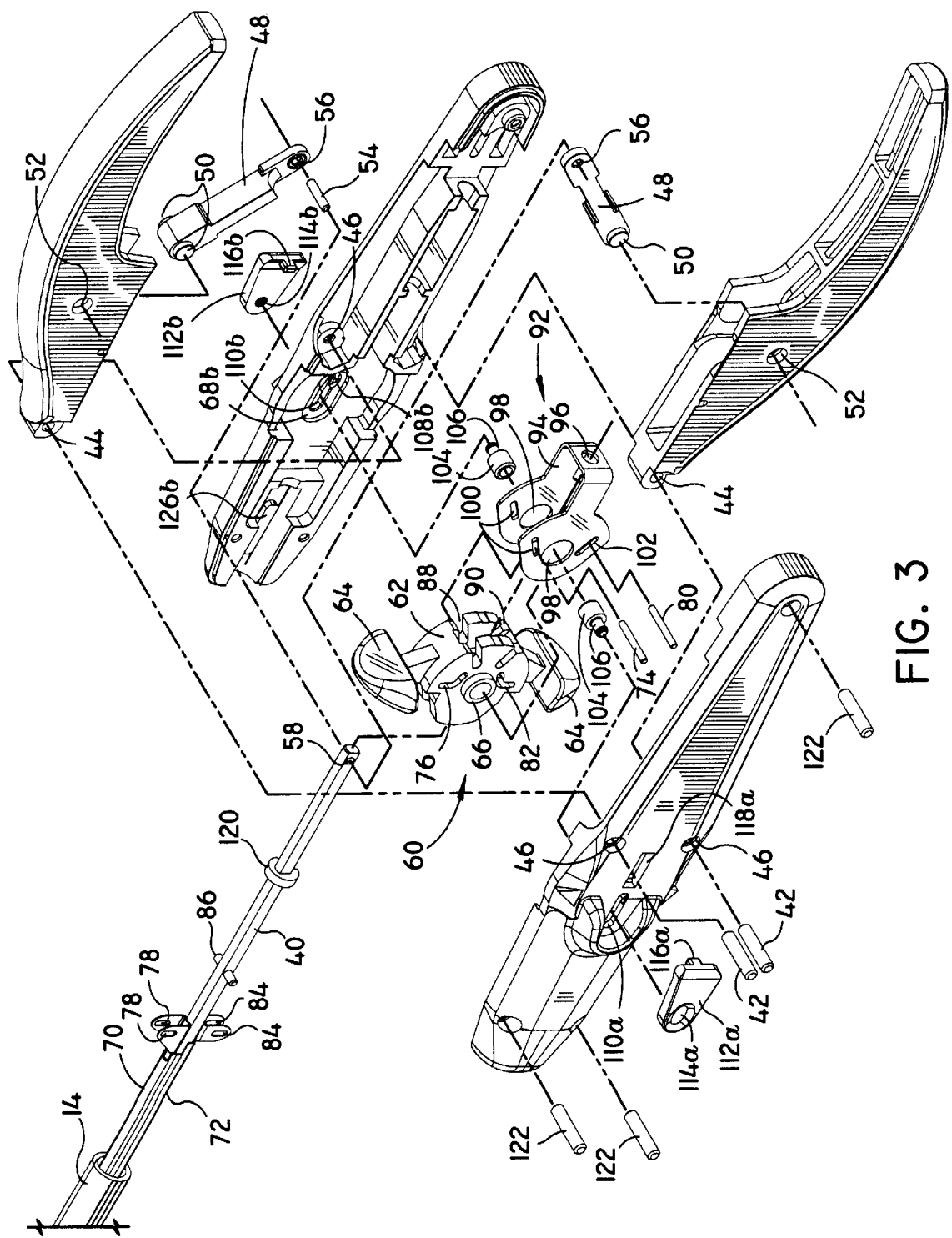
FIG. 3 is a perspective view, with parts separated, of the handle portion of the surgical suturing apparatus of FIG. 1.

Referring now in general to FIGS. 1 and 2 and in particular to FIG. 3, in order to open and close movable jaw 18 relative to stationary jaw 16, surgical suturing apparatus 10 is provided with a center rod 40 which extends through body portion 14 into handle housing 12. As noted above, handles 20 are movably mounted to housing halves 12a and 12b to move movable jaw 18 relative to stationary jaw 16. Specifically, handles 20 are pivotally mounted to handle housing 12 by means of handle screws 42 which function as pivot pins and which extend through handle holes 44 and into pivot holes 46 formed in housing halves 12a and 12b. Handles 20 are connected to center rod 40 by means of a pair of links 48. Projections 50 at a distal end of links 48 engage holes 52 formed in handles 20 while a proximal end of links 48 are affixed to a proximal end of center rod 40 by means of a pin 54. Pin 54 extends through holes 56 and links 48 and through a center rod hole 58 in center rod 40. Thus, by pivoting handles 20 relative to housing halves 12a and 12b center rod 40 is reciprocated within body portion 14. Specifically, as handles 20 are closed toward handle housing 12, links 48 draw center rod 40 proximally to close movable jaw 18 against stationary jaw 16, while moving handles 20 away from handle housing 12 causes links 48 to force center rod 40 distally to open movable jaw 18 away from stationary jaw 16, in a manner described in more detail hereinbelow.

As noted above, surgical suturing apparatus 10 includes a securing mechanism 22 for releasably securing a surgical needle in either stationary jaw 16 or movable jaw 18. Securing mechanism 22 generally includes a reciprocating mechanism 60 having a toggle wheel 62 pivotally mounted between housing halves 12a and 12b. Toggle wheel 62 includes a pair of thumb levers 64 extending outwardly of handle housing 12. Toggle wheel 62 is rotatably mounted between handle housings 12a and 12b by a pair of mounting projections 66 which reside in slots 68a and 68b formed in housing halves 12a and 12b.

Securing mechanism 22 further includes a pair of upper and lower channel members 70 and 72 which extend through body portion 14 and which are provided to transmit the motion of toggle wheel 62 to the jaws and assist in securing a surgical needle within stationary jaw 16 and movable jaw 18, respectively. Upper channel member 70 is affixed to toggle wheel 62 by means of a pin 74 which resides within a drive slot 76 formed in toggle wheel 62. Pin 74 extends through a hole 78 in the proximal end of upper channel member 70. Similarly, lower channel member 72 is affixed to toggle wheel 62 by means of a pin 80 which extends through a drive slot 82 formed in toggle wheel 62 and through a hole 84 formed in lower channel member 72. Thus, by rotating toggle wheel 62 within handle housing 12, upper and lower channel members, 70 and 72, respectively, are alternately reciprocated within body portion 14 so as to alternately secure a surgical needle within stationary jaw 16 or movable jaw 18 in a manner discussed in more detail below.

Surgical suturing apparatus 10 additionally includes locking structure which prevents movement of toggle wheel 62 when center rod 40 is in a distalmost position with movable jaw 18 spaced from stationary jaw 16. Specifically, center rod 40 includes a pin 86 which engages an upper notch 88 in toggle wheel 62 when toggle wheel 62 is rotated to place upper channel member 70 is in a proximalmost position and lower channel member 72 is in a distalmost position. Engagement of pin 86 within upper notch 88 prevents rotation of toggle wheel 62 to secure a needle in movable jaw 18. Conversely, when the surgical needle is secured in stationary jaw 16 and upper channel member 70 is in a distalmost position with lower channel member 72 in a proximalmost position, pin 86 engages a lower notch 90 formed on toggle wheel 62 and prevents rotation thereof. Further, when handles 20 are compressed against handle housing 12 to thereby draw center rod 40 to a proximal position, pin 86 is moved out of either upper notch 88 or lower notch 90 and allows free rotation of toggle wheel 62. This corresponds to a condition when movable jaw 18 is closed against stationary jaw 16.

In order to load a surgical needle into stationary jaw 16 and/or movable jaw 18, it is necessary to be able to move upper and lower channel members 70, 72, respectively, simultaneously in a distal direction for reasons described hereinbelow. Thus, as noted above, surgical suturing apparatus 10 is provided with loading mechanism 24 which includes lock override structure 92. Lock override structure 92 enables toggle wheel 62 to be slid distally within housing halves 12a and 12b. Specifically, toggle wheel 62 is suspended on a U-shaped channel 94. Channel 94 has a hole 96 for clearance of center rod 40 therethrough and holes 98 for receipt of projections 66. U-shaped channel 94 has upper slots 100 and lower slots 102 for sliding receipt of pins 74 and 80. Toggle wheel 62 and U-shaped channel 94 are secured in a fixed position with respect to housing halves 12a and 12b by means of a pair of plungers 104. Plungers 104 have reduced diameter knobs 106 extending therefrom. Plungers 104 reside in holes 108a and 108b formed in housing halves 12a and 12b, respectively. A pair of slots 110a and 110b extend distally from holes 108a and 108b. By depressing plungers 104 inwardly against housing halves 12a and 12b, plungers 104 clear holes 108a and 108b and allow knobs 106 to ride distally within slots 110a and 110b thereby moving the entire needle securing mechanism 22 distally within surgical suturing apparatus 10. A pair of slides 112a and 112b are provided on an outer surface of housing halves 12a and 12b and include holes 114a and 114b for receipt of knobs 106. Tabs 116a and 116b on slides 112a and 112b ride longitudinally within slots 118a and 118b formed on housing halves 12a and 12b.

In order to bias handles 20 away from housing halves 12a and 12b and thereby bias the jaw structure to an open position, there is provided a C-ring 120 fixedly mounted to center rod 40. C-ring 120 is provided to provide an abutment surface for a spring (not shown) which biases center rod 40 into a proximalmost position corresponding to an open jaw condition. Additionally, housing halves 12a and 12b are preferably secured together by means of housing halves screws 122. While illustrated as being secured by screws 122, housing halves 12a and 12b may be secured by any other suitable means, such as, for example, adhesives, welding, etc.

Figure 4:
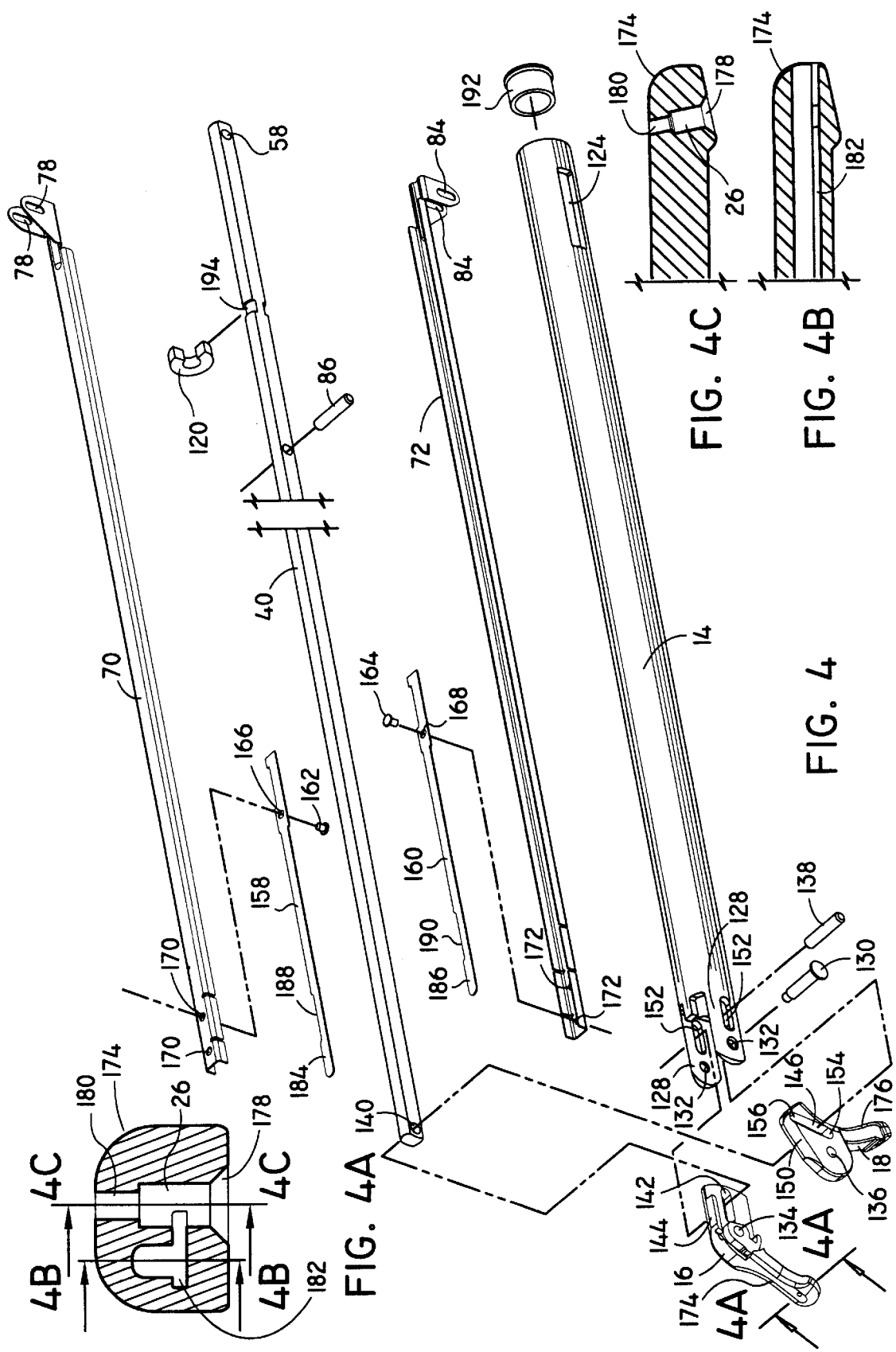
FIG. 4 is a perspective view, with parts separated, of the distal portion of the surgical suturing apparatus of FIG. 1.

Referring now to FIG. 4, and as noted above, body portion 14 extends distally from handle housing 12 and is affixed thereto. Specifically, body portion 14 includes a pair of housing slots 124 which are configured to engage body projections 126a and 126b formed on housing halves 12a and 12b respectively (see FIG. 3).

As noted above, stationary jaw 16 and movable jaw 18 are mounted on a distal end of body portion 14. The distal end of body portion 14 includes a pair of distally projecting jaw support arms 128. Stationary jaw 16 and movable jaw 18 are secured to the distal end of body portion 14 by a jaw support pin 130 which extends through holes 132 in jaw support arms 128 and through holes 134 and 136 in stationary jaw 16 and movable jaw 18, respectively.

As further noted above, center rod 40 is provided to reciprocate longitudinally within body portion 14 in order to open and close movable jaw 18 with respect to stationary jaw 16. Thus, center rod 40 is provided with a pivot pin 138 which is affixed within a hole 140 at a distal end of center rod 40. Pivot pin 138 is positioned within a straight slot 142 formed in a mounting portion 144 of stationary jaw 16 and extends into an angled slot 146 formed in a mounting portion 150 of movable jaw 18. Center rod 40 along with pivot pin 138 is stabilized in its longitudinal reciprocation within body portion 14 as pivot pin 138 rides within a pair of longitudinal slots 152 formed in jaw support arms 128.

Thus, as center rod 40 is moved to a distalmost position, driving pivot pin 138 to a first end 154 of angled slot 146, jaw 18 is forced to an open position spaced apart from stationary jaw 16. Conversely, as center rod 40 is drawn proximally within body portion 14, pivot pin 138 is pulled to a second end 156 within angled slot 146 to thereby pivot movable jaw 18 to a closed position substantially adjacent or in close cooperative alignment with stationary jaw 16. Straight slot 142 is aligned with the longitudinal axis of center rod 40 so that movement of center rod 40 drives pivot pin 138 within straight slot 142. This particular alignment of straight slot 142 allows stationary jaw 16 to remain stationary as center rod 40 is reciprocated. However, it is specifically contemplated that the stationary jaw 16 be movable relative to body portion 14. This is easily accomplished by angling the alignment of straight slot 142 so that movement of pivot pin 138 within slot 142 moves stationary jaw 16 in the same manner as movable jaw 18.

Securing mechanism 22, which, as noted above, is provided for alternately securing a surgical needle within either of stationary jaw 16 or movable jaw 18, additionally includes upper and lower needle securing blades 158 and 160. Preferably, upper and lower needle securing blades 158 and 160 are secured to upper and lower channel members 70, 72 by means of blade pins 166 and 168. However, other means of connecting blades 158 and 160 to channel members 70, 72 are contemplated. Specifically, an upper pin 162 extends through a blade hole 166 in upper needle securing blade 158 and through one of channel holes 170 in channel member 70. Similarly, a lower pin 164 extends through a blade hole 168 in lower needle securing blade 160 and is affixed to channel 72 by extending through one of channel holes 172. Thus, as reciprocating mechanism 60 is moved, channel members 70, 72 alternately reciprocate upper and lower needle securing blades 158, 160. More specifically, upper and lower needle securing blades 158, 160 are reciprocated within tissue gripping portions 174 and 176 of stationary jaw and movable jaw 16, 18, respectively.

Referring now to FIGS. 4a–4c, the details of a tissue gripping portion of a jaw, for example, tissue gripping portion 174 of stationary jaw 16, will now be described. As noted above, each jaw structure includes a needle receiving recess, for example, needle receiving recess 26 in tissue gripping portion 174 of stationary jaw 16. Needle receiving recess 26 includes a flared end 178 to aid in guiding a surgical needle into tissue receiving recess 26 and a narrow or reduced area portion 180 to prevent a surgical needle from passing completely through needle receiving recess 26.

Additionally, tissue gripping portion 174 of jaw 16 includes a blade slot 182 extending the length of tissue gripping portion 174. Blade slot 182 is configured to slidingly receive upper needle securing blade 158 therein. While not specifically illustrated, movable jaw 18 includes a corresponding flared end and a reduced area portion in needle receiving recess 28. Further, movable jaw 18 additionally includes a longitudinally extending blade slot 196 (FIG. 19), intersecting needle receiving recess 28, for sliding receipt of lower needle securing blade 160.

As shown in FIG. 4A, blade slot 182 in stationary jaw 16 intersects needle receiving recess 26. In order to secure a surgical needle in one of the jaw structures, for example, upper jaw 16, upper needle securing blade 158 is advanced distally through blade slot 182 until a needle engaging edge 184 (FIG. 4) of upper needle securing blade 158 engages corresponding structure in a surgical needle (See FIGS. 16 and 17). To release the surgical needle from stationary jaw 16, upper needle securing blade 158 is retracted proximally until needle securing edge 184 no longer engages the surgical needle in the intersecting portion of blade slot 182 and needle receiving recess 26. Similarly, lower needle securing blade 160 includes a needle engaging edge 186 (FIG. 4) which, when advanced into the corresponding juncture of its blade slot 196 and needle receiving recess 28, engages corresponding structure on the surgical needle and firmly engages the surgical needle in movable jaw 18. It should be noted that whenever needle securing blade 158 is in a distalmost position securing a surgical needle within stationary jaw 16, needle securing blade 160 is in a proximalmost position within movable jaw 18 remote from recess 28, and visa-versa.

In order to facilitate loading a surgical needle into one or both of the stationary jaw 16 and movable jaw 18, upper and lower needle securing blades 158 and 160 are provided with loading recesses 188 and 190 respectively. As noted above, when the toggle wheel is moved distally within housing halves 12a and 12b, channel members 70, 72 move distally thereby moving needle securing blades 158, 160 distally within the corresponding slots in upper jaw 16 and lower jaw 18. This corresponds to a position where loading recesses 188 and 190 are adjacent needle receiving recesses 26 and 28, respectively, and therefore cannot block or engage any structure of the needle.

A hub 192 may be provided at a proximal end of body portion 14 to assist in stabilizing body portion 14 with respect to housing handle 12 and insure an appropriate seal. Further, C ring 120 is mounted about a reduced area portion 194 of center rod 40.

Figure 5:
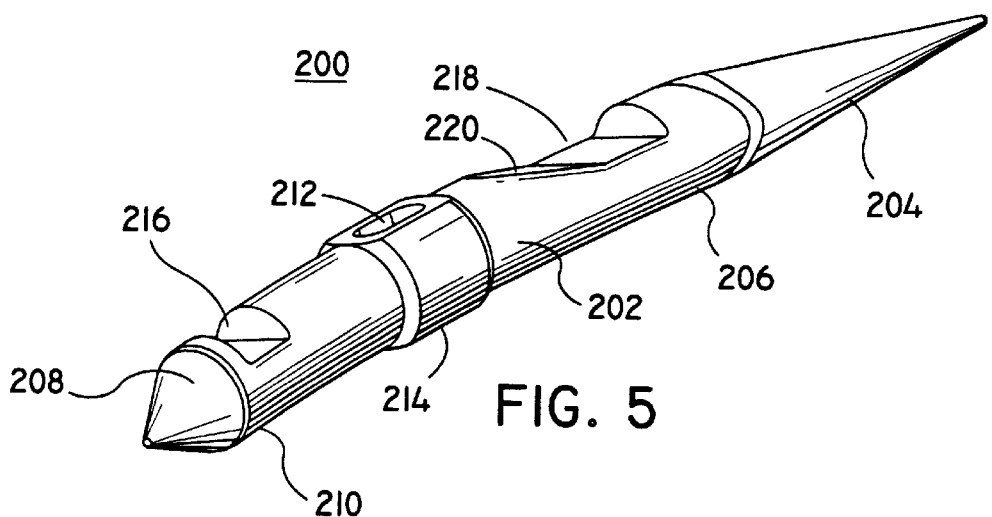
FIG. 5 is a perspective view of a surgical suturing needle.
Figure 6:
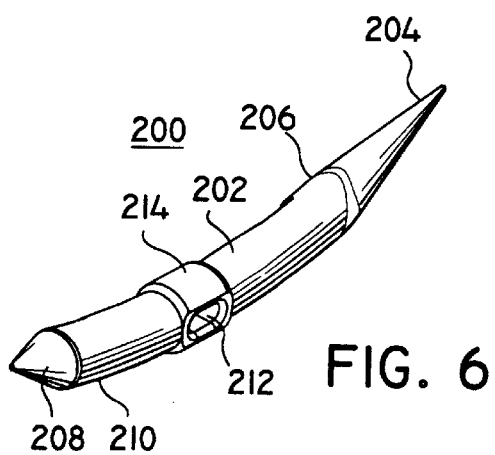
FIG. 6 is another perspective view of the surgical suturing needle.
Figure 7:
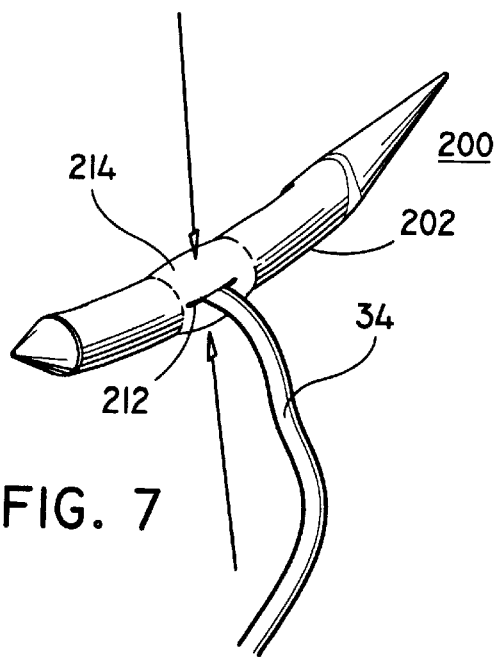
FIG. 7 is a perspective view of the surgical suturing needle with a length of suture material being secured thereto.

Referring now to FIGS. 5–7, a novel surgical needle 200 suitable for use with surgical suturing apparatus 10 and particularly suited for use in heart valve replacement surgery will now be described. Surgical needle 200 generally includes a curved body portion 202 having an elongated penetrating portion 204 extending from a first end 206 of body portion 202. A pointed portion 208 is formed adjacent a second end 210 of body portion 202. Elongated penetrating portion 204 is particularly useful to facilitate penetrating tough material, such as for example, plastics or fabric meshes of the type employed in heart valve replacement structures. Body portion 202 additionally includes a suture receiving aperture 212 for receiving length of suture material 34. A bulge 214 is formed adjacent suture receiving aperture 212 such that when an end of length of suture material 34 is inserted within suture receiving aperture 212, bulge 214 may be inwardly compressed to thereby secure length of suture material 34 within suture receiving aperture 212 (FIG. 7). By providing additional material in the form of bulge 214, after compression, body portion 202 retains a relatively uniform outer diameter.

As noted above, surgical suturing apparatus 10 is particularly designed to alternately pass surgical needle 200 between stationary jaw 16 and movable jaw 18. Thus, apparatus receiving structure in the form of a first blade receiving recess 216 and a second blade receiving recess 218 are formed within body portion 202. First blade receiving recess 216 has a generally symmetrical cross-section and is configured to receive needle engaging edge 184 of upper needle securing blade 158 to thereby secure surgical needle 200 within stationary jaw 16. In order to pass surgical needle 200 to movable jaw 18, second blade receiving recess 218 is configured to receive needle engaging edge 186 of lower needle securing blade 160 to thereby secure surgical needle 200 within movable jaw 18. Second blade securing recess 218 is of an asymmetrical cross-section having a chamfered edge portion 220. Chamfered edge portion 220 is provided to prevent surgical needle 200 from engaging or "hanging up" on heart valve tissue or structure material as surgical needle 200 is forced therethrough.

Figure 8:
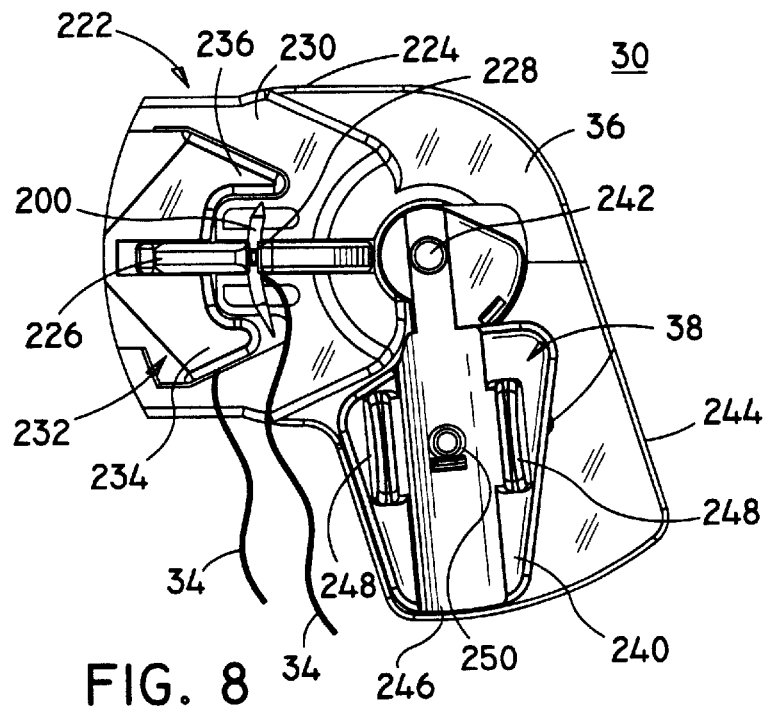
FIG. 8 is a top plan view of a disposable loading unit with surgical needles mounted thereon.
Figure 9:
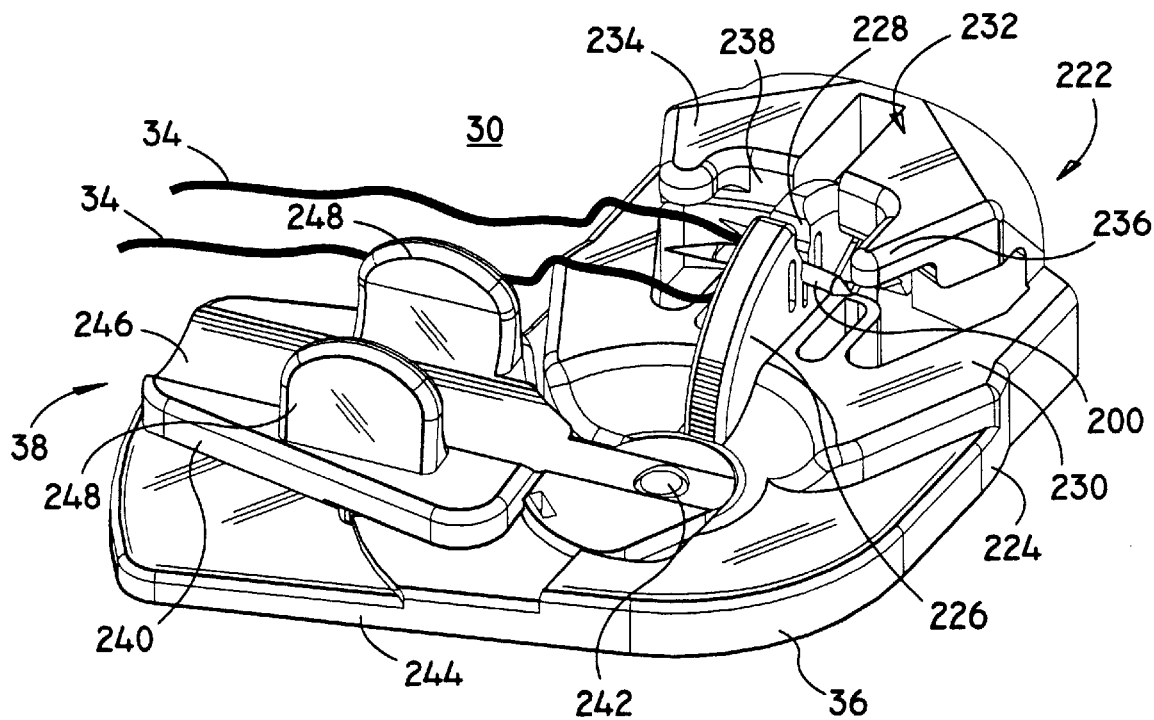
FIG. 9 is a perspective view of the loading unit of FIG. 8.

Referring now to FIGS. 8-11, novel disposable loading unit 30 is provided for supplying one or more surgical needles 200 to surgical suturing apparatus 10. More particularly, loading unit 30 is provided to precisely position the angled jaw structure of surgical suturing apparatus 10 about surgical needle 200 to facilitate loading therein. Referring initially to FIGS. 8 and 9, and as noted above, loading unit 30 generally includes body portion 36 having apparatus receiving structure 38 thereon. Body portion 36 includes a needle supply station 222 formed in a first portion 224 of body portion 36. Needle supply station 222 is provided to align and maintain a surgical needle 200 in a position to be grasped by jaws 16 and 18 of surgical suturing apparatus 10.

Needle supply station 222 further includes a needle support member 226 which securely and releasably retains one or more surgical needles 200 within a first slot 228 formed therein. Surgical needle 200 is held within first slot 228 in friction fit fashion. A shelf 230 is formed in first portion 224 of body portion 36 to maintain stationary jaw 16 and movable jaw 18 at a predetermined level such that surgical needle 200, disposed within first slot 228, is in alignment with needle receiving recesses 26 and 28, in stationary jaw 16 and movable jaw 18, respectively.

Needle supply station 222 further includes a safety mechanism 232 which includes a pair of asymmetrical wings 234 and 236 projecting towards needle support member 226. A gap 238 defined between wings 234 and 236 allows jaws 16 and 18 surgical suturing apparatus to be lifted straight up out of loading unit 30 after surgical suturing apparatus has been loaded with surgical needle 200 and jaws 16 and 18 moved to a closed position. Wing 234 is shorter than wing 236 to provide clearance for the elongated penetrating portion 204 of surgical needle 200 as surgical suturing apparatus 10 is lifted clear of loading unit 30.

As noted above, loading unit 30 is provided with apparatus receiving structure 38 to receive a distal end of surgical suturing apparatus and position stationary jaw 16 and movable jaw 18 about surgical needle 200. Apparatus receiving structure 38 generally includes a swing base 240 which is pivotally mounted about a pivot pin 242 formed on a second portion 244 of base portion 36. Swing base 240 is configured to move through a predetermined arc of approximately 25 degrees relative to second portion 244 in order to move stationary jaw 16 into alignment about second end 210 of surgical needle 200. Swing base 240 includes an arcuate recess 246 for receipt of body portion 14 of surgical suturing apparatus 10. Additionally, swing base 240 includes a pair of side tabs 248 to maintain body portion 14 of surgical suturing apparatus 10 in alignment on swing base 240. To insure appropriate longitudinal positioning of body portion 14 within swing base 38, swing base 38 is provided with an alignment stud 250 positioned within arcuate recess 248 and configured to engage corresponding structure on body portion 14 of surgical suturing apparatus 10. This is particularly desirable in operations requiring more than one length of suture, for example, where a double needle or double armed suture with a pledget is utilized. More than two needle holding slots is contemplated.

Referring now to FIGS. 10 and 11, needle support member 226 is movably mounted within a slot 252 formed within first portion 224 of body portion 36. Needle support member 226 is preferably mounted for rotatable movement relative to body portion 36. A pair of projections 254 engage a hole 256 in needle support member 226 and allows needle support member 226 to rotate relative to body portion 36. As shown, apparatus receiving structure 38 is movable within a first plane and needle support member 226 is movable within a second plane substantially perpendicular to the first plane.

Figure 11B:
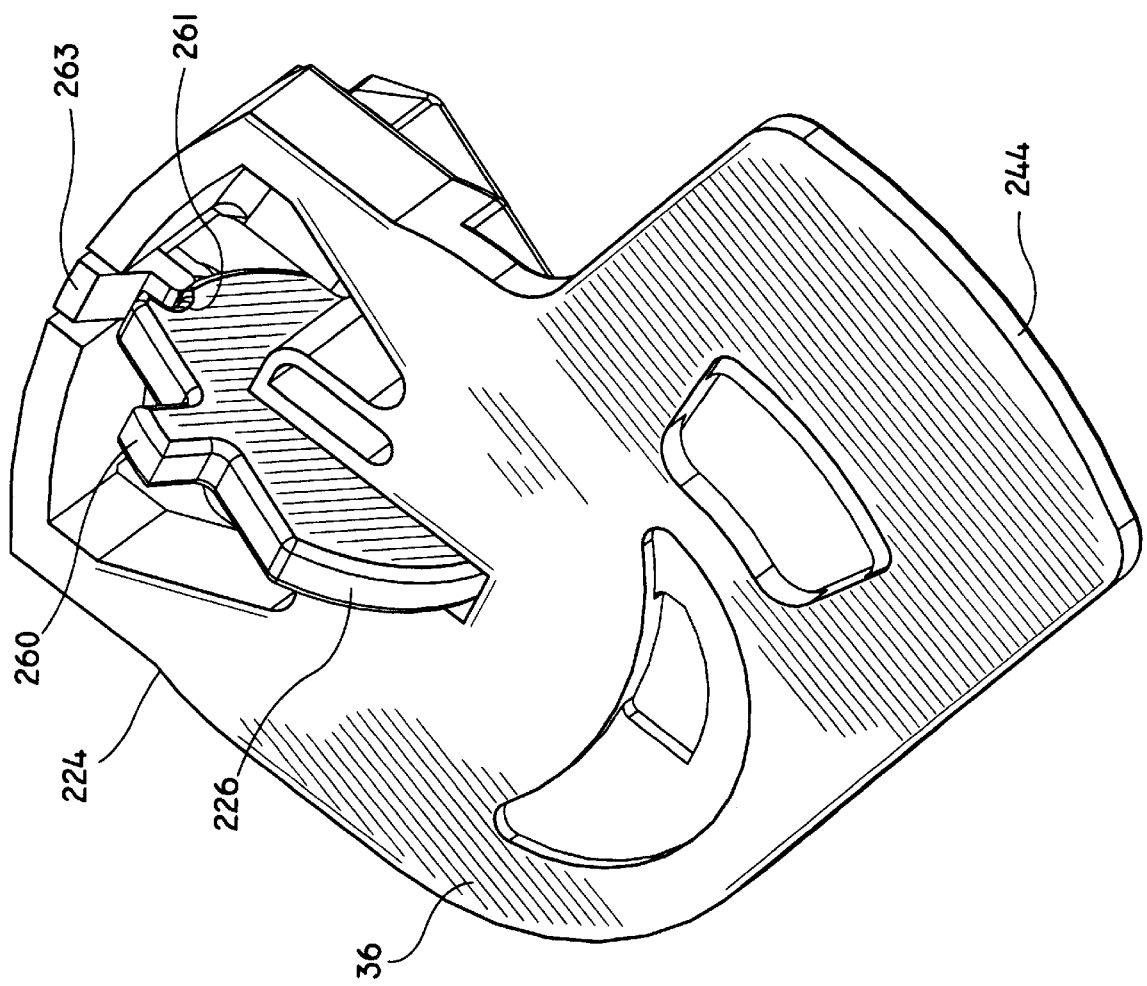
FIG. 11B is a view similar to FIG. 11A, with a needle support member rotated from a first position to a second position.

As noted hereinabove, disposable loading unit 30 is provided to supply one or more surgical needles 200 for use within surgical suturing apparatus 10. Thus, needle support member 226 may be provided with a second slot 258 to retain a second surgical needle 200 in friction fit fashion therewithin. A tab 260 at the base of needle support member 226 is provided to rotate needle support member between a first position aligning first surgical needle 200 held within first slot 228 in a position to be grasped by surgical suturing apparatus 10 and a second position which would align a surgical needle 200 held within second slot 258 in a position to be grasped by surgical suturing apparatus 10. As shown in FIGS. 10, 11A and 11B, needle support member includes detents 259 and 261 which cooperate with a flexible detent lock 263 formed on body portion 36 to lock needle support member 222 in either the first (FIG. 11A) or second (FIG. 11B) positions.

As noted above, swing base 240 is movably mounted within respect to body portion 36. Pivot pin 242 extends through a hole 262 formed in swing base 240. A first L-shaped tab 264 is provided on an underside of swing base 240 and engages a first slot 266 to secure swing base 240 to base portion 36 and guide swing base 240 in its arcuate motion thereon. A second L-shaped tab 268 is also formed on an underside of swing base 240 and rides within a second slot 270. In addition to assisting in securing swing base 240 to base portion 36, second L-shaped tab 268 limits the travel of swing base 240 during its arcuate motion. Additionally, a detent 272 is formed in an underside of swing base 240 and engages a projection 274 formed on second portion 244 of base portion 36 to hold swing base 240 in an initial position to receive surgical suturing apparatus 10.

While length of suture material 34 is illustrated as extending from needle 200 off loading unit 30, it is also contemplated that length of suture material 34 may be stored on various retaining structures, such as, for example, reels, cavities, racetracks, etc. provided on or within loading unit 30.

Figure 12:
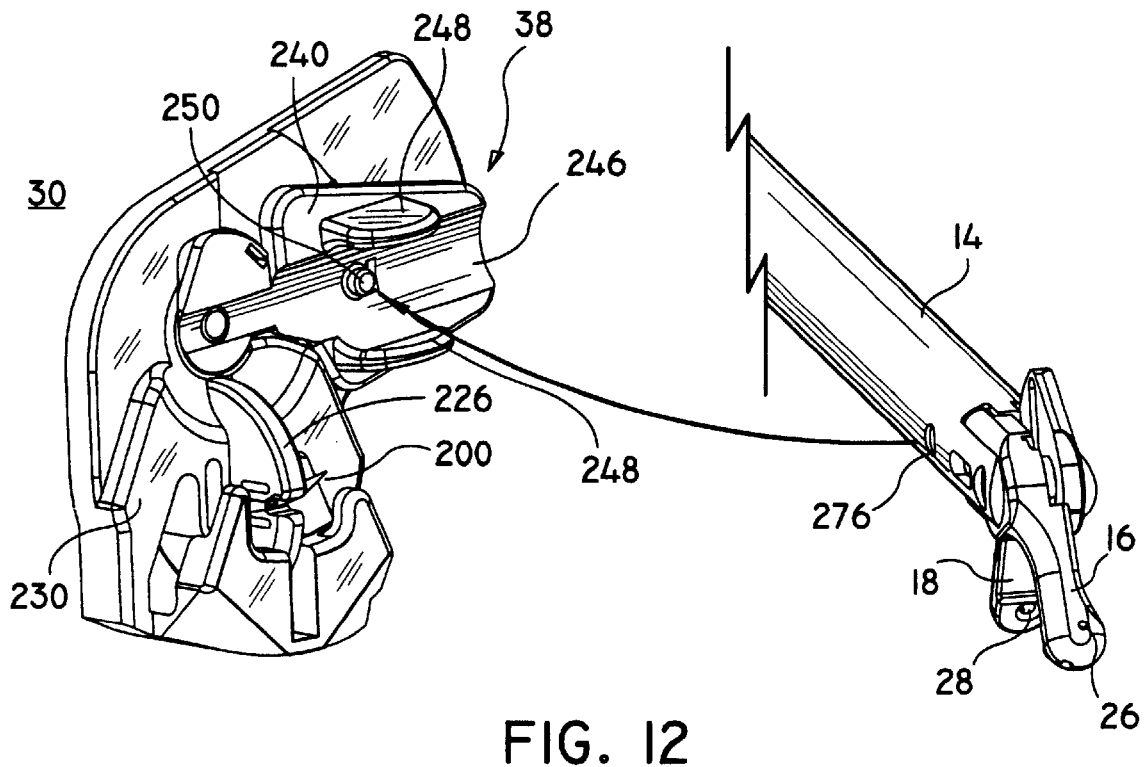
FIG. 12 is a perspective view of the loading unit of FIG. 8 and the distal end of the surgical suturing apparatus in preparation for mounting the surgical suturing apparatus on the loading unit.
Figure 13:
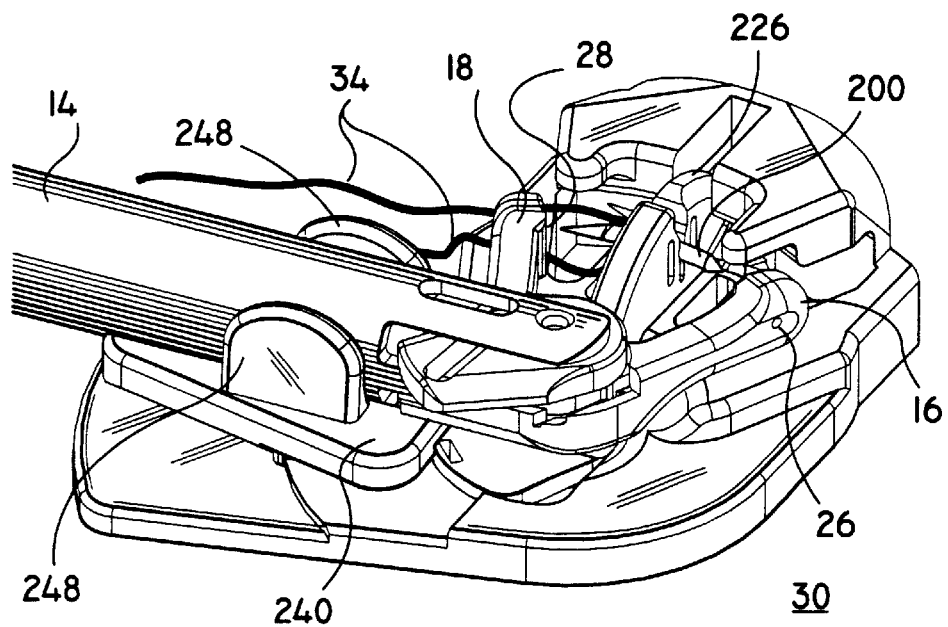
FIG. 13 is a perspective view of the distal end of the surgical suturing apparatus positioned on the disposable loading unit in preparation for loading a needle.

Referring now to FIGS. 12–15, the process of loading surgical needle 200 from disposable loading unit 30 and into the jaw structure of surgical suturing apparatus 10 will now be described. Referring initially to FIGS. 12 and 13, body portion 14 of surgical suturing apparatus 10 is positioned within arcuate recess 246 of apparatus receiving structure 38 such that a hole 276 in body portion 14 is positioned over alignment stud 250 and body portion 14 is frictionally gripped between side tabs 248. Thus positioned, stationary jaw 16 and movable jaw 18 lie against support shelf 230 and are in a position to insure proper alignment of needle receiving recesses 26 and 28 with elongated penetrating portion 204 and pointed portion 208 of surgical needle 200. Surgical needle 200 can now be loaded in jaws 16 and 18 by moving jaws 16 and 18 about surgical needle 200.

Figure 15:
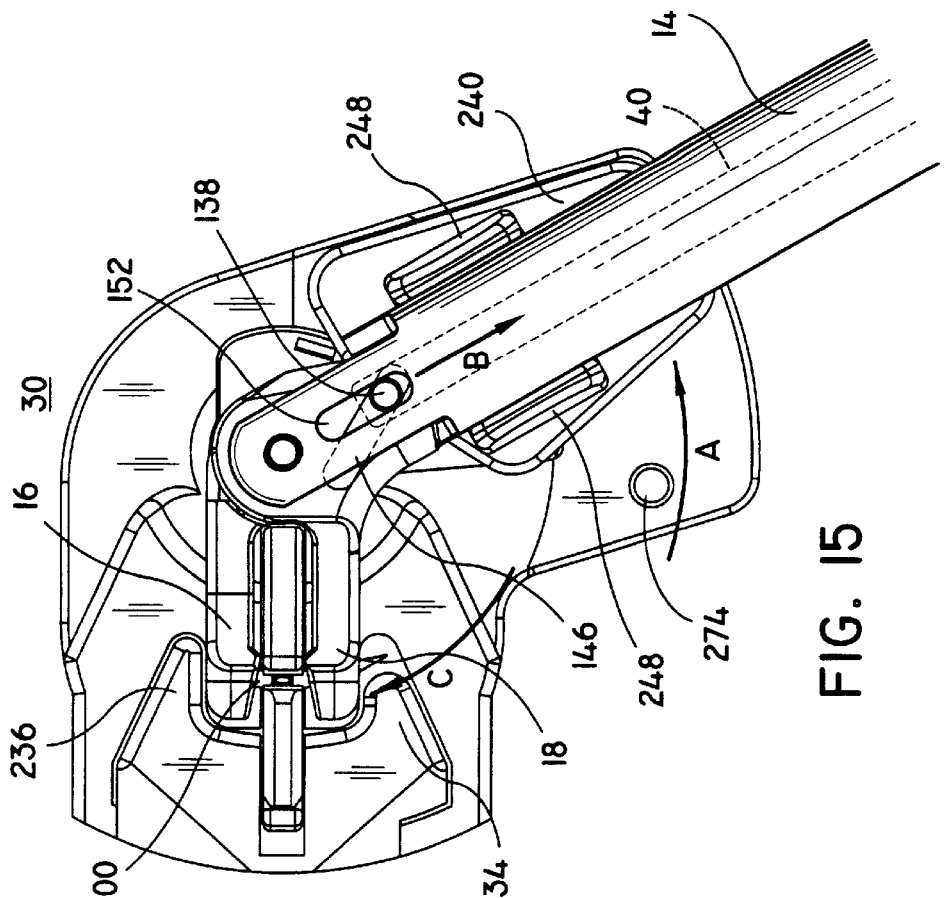
FIG. 15 is a top plan view illustrating the installation of a surgical needle into the jaw structure of the surgical suturing apparatus.
Figure 14:
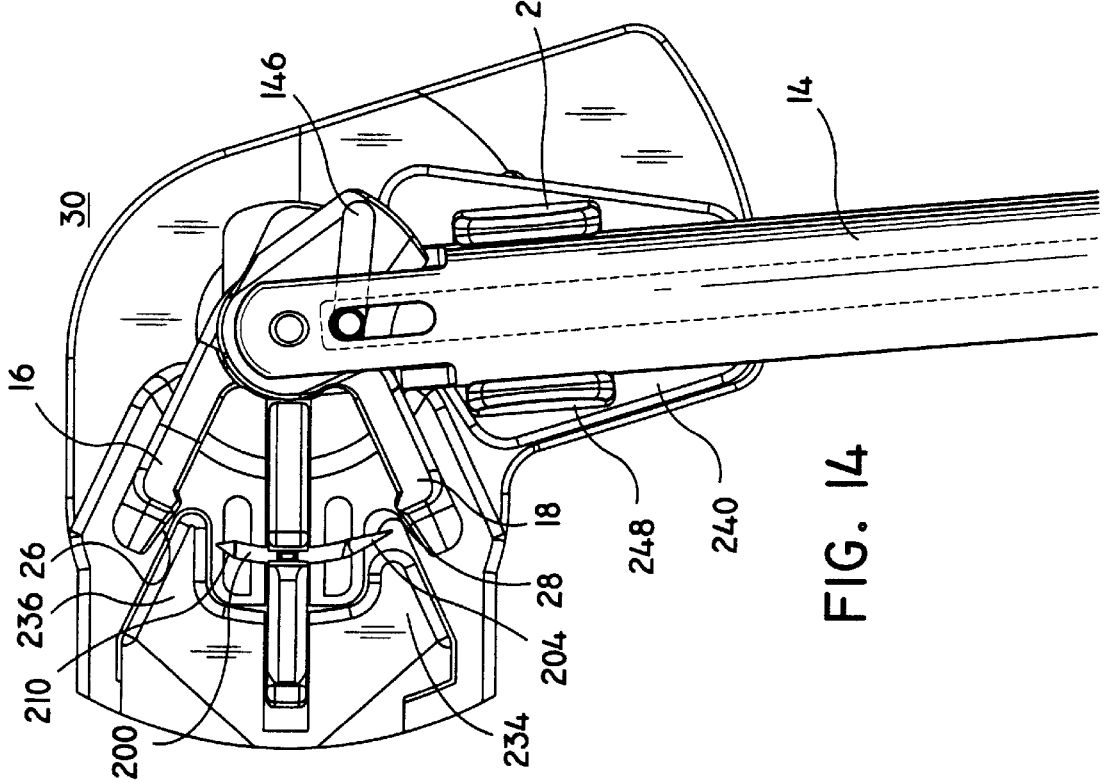
FIG. 14 is a top plan view of the distal end portion of the surgical suturing apparatus on the disposable loading unit and corresponding to FIG. 13.

Referring now to FIGS. 14 and 15, in one method of closing stationary jaw 16 and movable jaw 18 about surgical needle 200, tubular body portion 14, positioned on swing base 240, is moved in the direction of arrow A to bring needle receiving recess 26 of stationary jaw 16 about second end 210 of surgical needle 200. Either simultaneously or subsequently, handles 20 are closed to draw center rod 40 in a proximal direction indicated by arrow D thereby moving pin 138 within angled slot 146 of movable jaw 18 thus moving movable jaw 18 in the direction of arrow C to position needle receiving recess 28 of movable jaw 18 about the elongated penetrating portion 204 of surgical needle 200. Preferably, however, squeezing handles 20 together closes jaws 16 and 18 relative to each other over surgical needle 200 and automatically swings body portion 14 in the direction of arrow A relative to body portion 36 of loading unit 30. In this manner, surgical needle 200 is precisely positioned within needle receiving recesses 26 and 28 of stationary jaw 16 and movable jaw 18.

Once surgical needle 200 has been positioned needle receiving recesses 26 and 28, toggle wheel 62, which had previously been moved to the distal loading position in the manner described hereinabove, may be pulled proximally to cause needle engaging edges 184 and 186 of upper and lower needle securing blades 158 and 160 respectively, into engagement with first and second blade receiving recesses 216 and 218 formed in surgical needle 200.

With the jaws in a closed position and surgical needle 200 secured within one or both of stationary jaw 16 and movable jaw 18, surgical suturing apparatus 10 may be lifted straight up out of loading unit 30. As noted hereinabove, safety mechanism 232 including wings 234 and 236 prevent this removal of surgical suturing apparatus 10 prior to stationary jaw 16 and movable jaw 18 being closed and securely positioned about surgical needle 200. Once so positioned, jaws 16 and 18 may be lifted up through gap 238 formed between wings 234 and 236.

Figure 16:
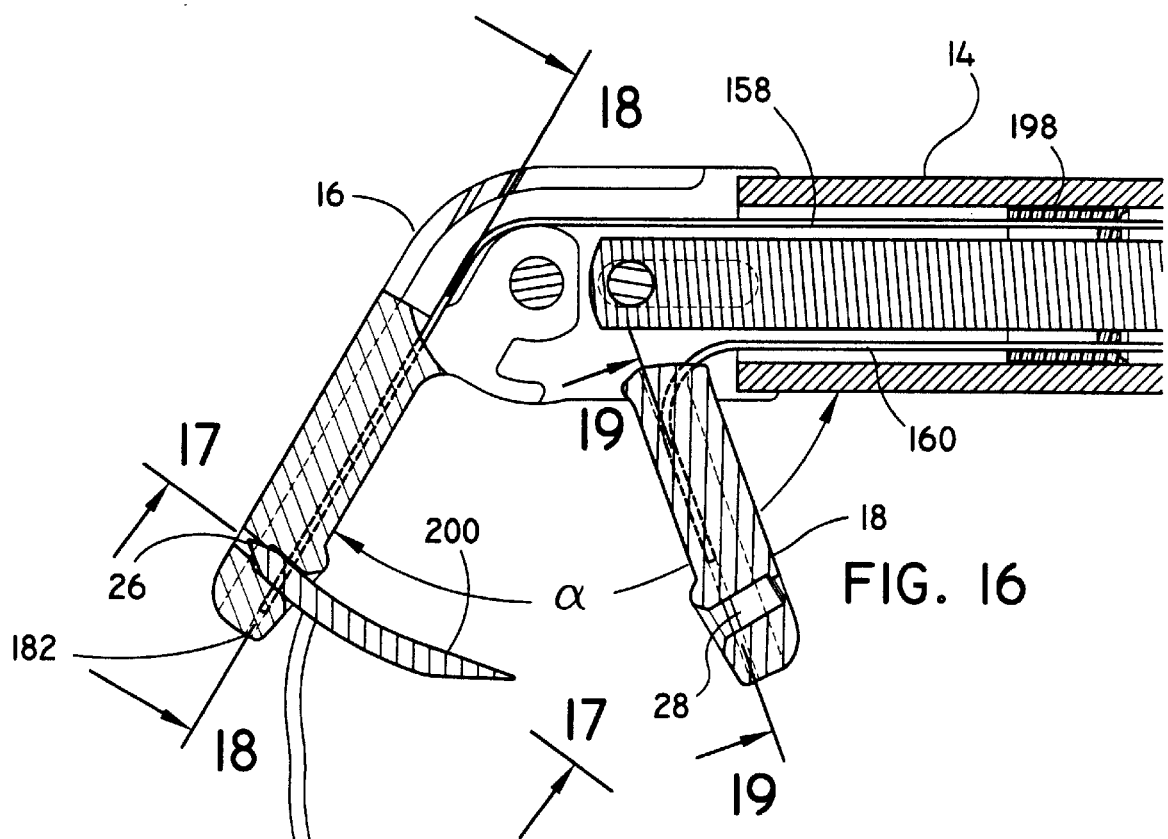
FIG. 16 is a cross-sectional view of the distal end portion of the surgical suturing apparatus with the surgical needle secured within a stationary jaw.
Figure 17:
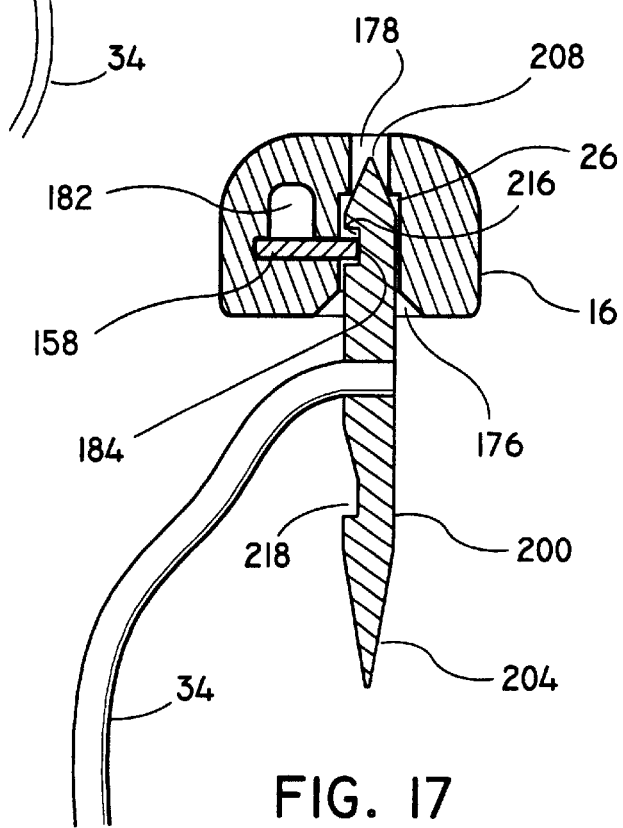
FIG. 17 is a sectional view taken along line 17—17 of FIG. 16.
Figure 18:
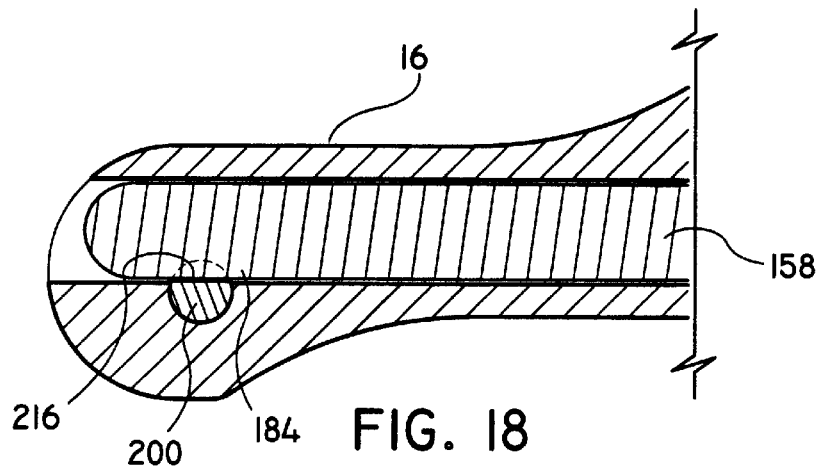
FIG. 18 is a sectional view taken along line 18—18 of FIG. 16.

Referring now to FIGS. 16 and 17 and as indicated above, in order to secure surgical needle 200 within stationary jaw 16, toggle wheel 64 is rotated so as to advance channel 70 and thus move upper needle securing blade 158 into engagement with surgical needle 200. Specifically, as shown in FIG. 18, needle engaging edge 184 of upper needle securing blade 158 engages first blade receiving recess 216 formed within surgical needle 200.

Body portion 14 optionally may be provided with a seal 198 to prevent body fluids from entering body portion 14. Seal 198 may also function as a support to stabilize and guide upper and lower needle securing blades 158 and 160, respectively, within body portion 14.

Figure 19:
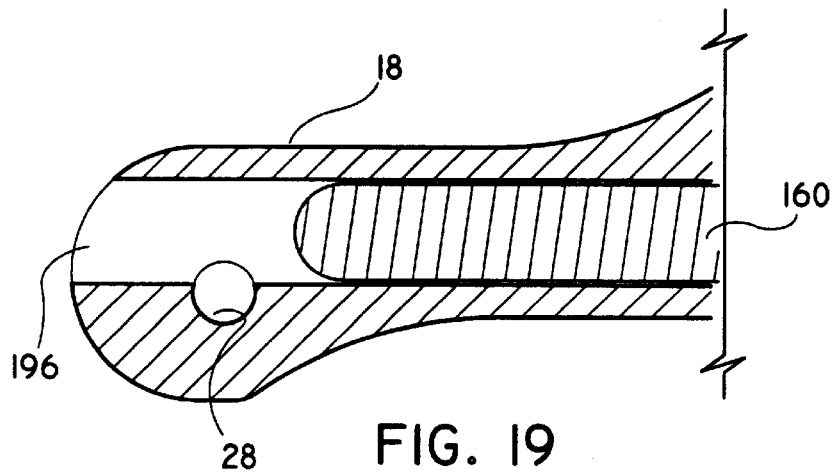
FIG. 19 is a sectional view taken along line 19—19 of FIG. 16.

FIG. 19 represents the condition of movable jaw 18 with lower needle securing blade 160 proximal in slot 196 relative to needle receiving recess 28 formed in movable jaw 18.

The procedure for using surgical suturing apparatus 10 and surgical needle 20 having length of suture material 34 attached thereto to a suture tissue sections will now be described. The following description is given during use of surgical suturing apparatus 10 to suture a heart replacement valve to tissue within the heart. As noted above, use of surgical suturing apparatus 10 in other procedures is specifically contemplated. In the following description, a heart valve cuff associated with a heart valve is illustrated being sutured to heart tissue. It will be appreciated that in actual surgery the complete heart valve will be in place within the cuff as the cuff is sutured to the heart tissue.

Figure 20:
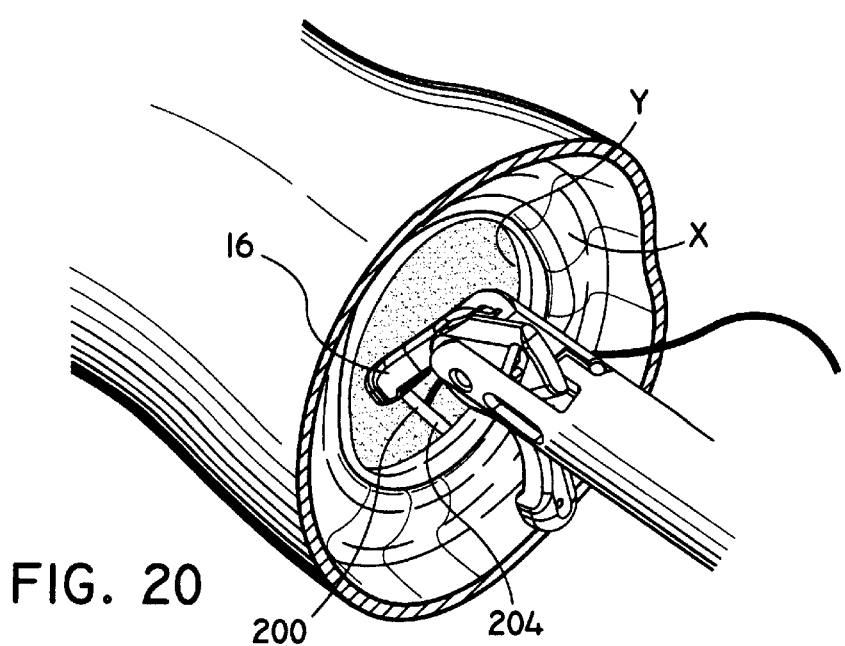
FIG. 20 is a perspective view of the distal end portion of the surgical suturing apparatus with surgical needle installed thereon being positioned adjacent a cuff of a heart valve structure and heart tissue.
Figure 21:
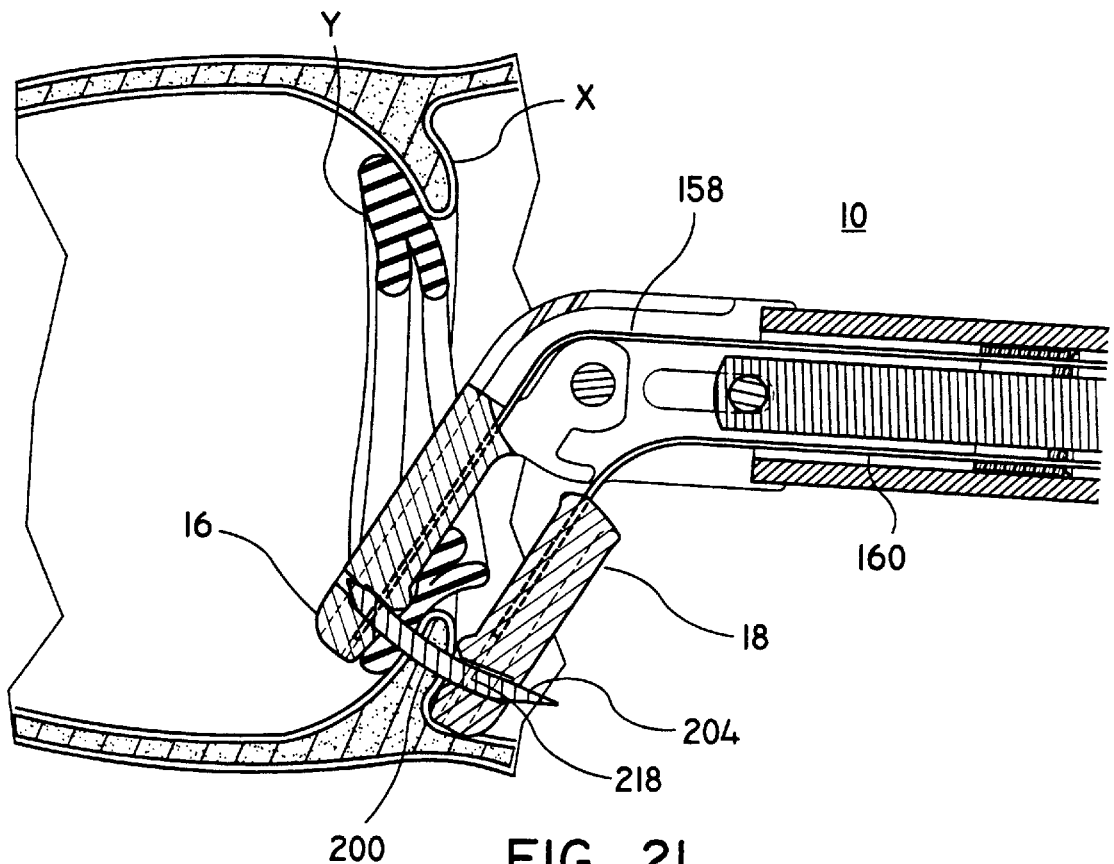
FIG. 21 is a sectional view illustrating the closing of the jaw structure and penetration of the surgical needle through the heart valve cuff structure and heart tissue.

Referring now to FIGS. 20–24, and initially to FIG. 20, as noted hereinabove, surgical needle 200 is initially positioned within stationary jaw 16 such that elongated penetrated portion 204 is axially aligned within the heart tissue and in a position to pierce a cuff Y associated with a replacement heart valve and a tissue section X. Referring now to FIG. 21, surgical suturing apparatus 10 is manipulated to force elongated penetrating portion 204 of surgical needle 200 through a tissue section X and a portion of a heart valve cuff Y.

Figure 22:
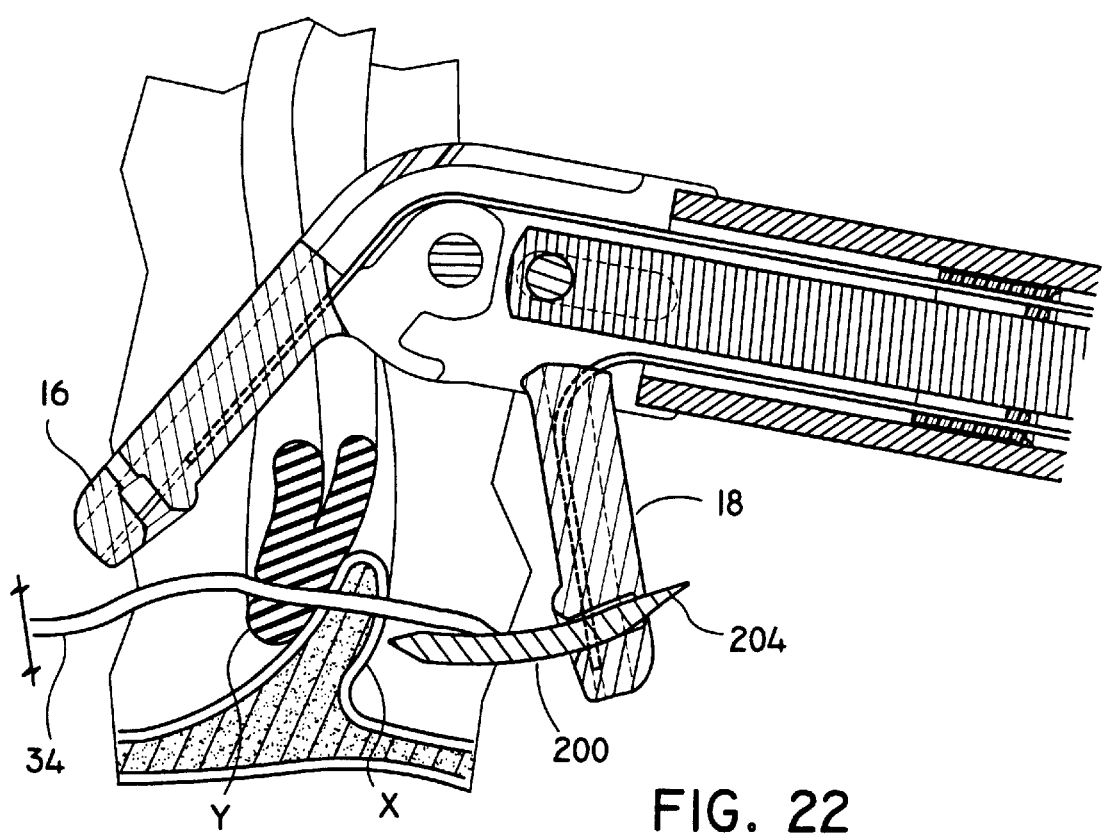
FIG. 22 is a view similar to FIG. 21 illustrating the opening of the jaw structure and drawing of the surgical needle and surgical suture through the heart valve cuff structure and heart tissue.

As shown in FIG. 21, surgical needle 200 is still engaged by upper needle securing blade 158 within stationary jaw 16. In order to transfer surgical needle 200 from stationary jaw 16 to movable jaw 18, toggle wheel 62 (FIG. 2) is reversed in its rotation so as to cause upper needle securing blade 158 to retract with channel 70 and cause lower needle securing blade 160 to advance with channel 72 and into engagement with second blade receiving recess 218. Referring to FIG. 22, once surgical needle 200 has been released from stationary jaw 16 and securely grasped by movable jaw 18, handles 20 are opened to allow movable jaw 18 to move away from stationary jaw 16 thereby draw the surgical needle 200 and attached length of suture material 34 through the tissue section X and heart valve material Y. As noted above, elongated penetrating portion 204 and chamfered edge portion 220 of surgical needle 200 facilitate passing surgical needle 200 through heart valve material Y.

Figure 23:
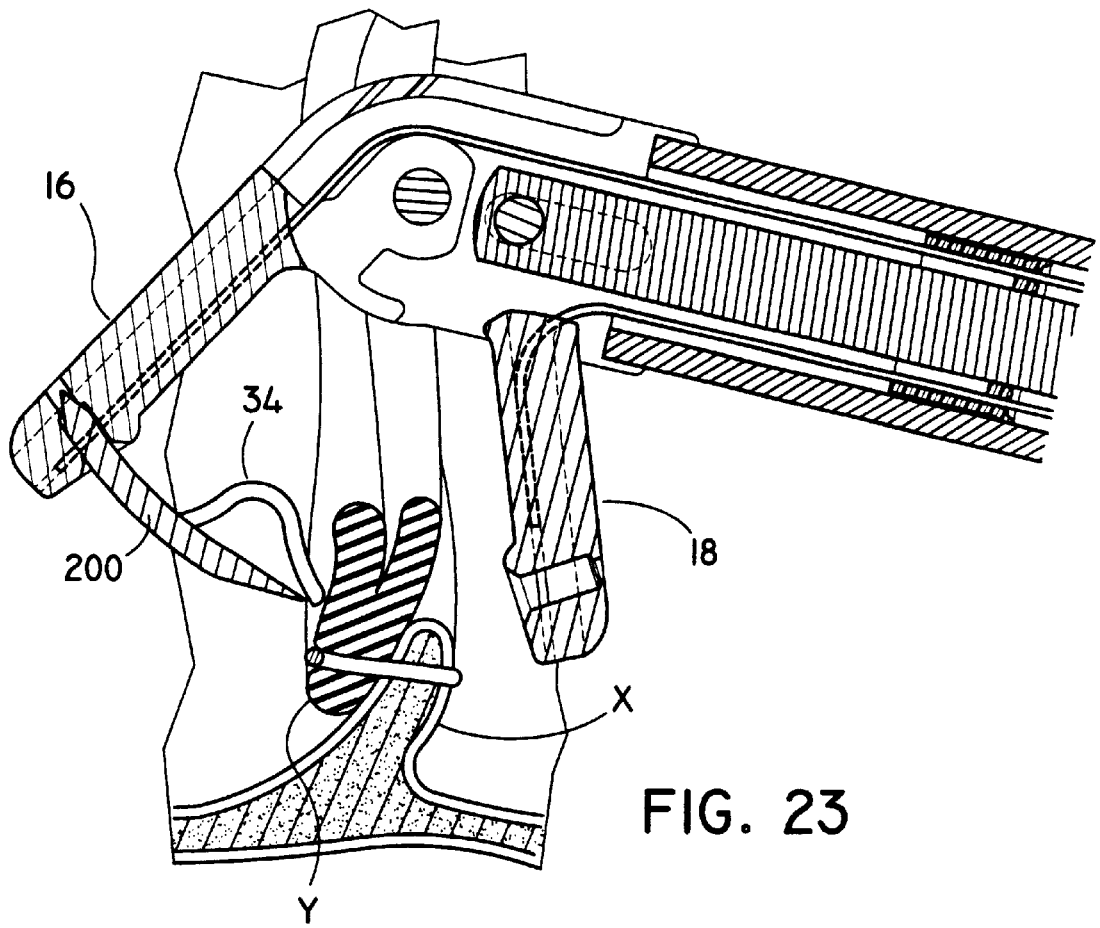
FIG. 23 is a sectional view of the distal end portion of the surgical suturing apparatus with the surgical needle again positioned in the stationary jaw structure and in position to re-pierce the heart valve cuff structure and heart tissue to form another stitch.

It should be noted that it is within the contemplated scope of the present disclosure to repenetrate a pair of tissues with pointed end 208 of surgical needle 200 and repeatedly pass surgical needle 200 between stationary jaw 16 and movable jaw 18. However, in the case of suturing through stiff material such as for example the heart valve cuff material Y, it is preferable to initially repass surgical needle 200 back to stationary jaw 16. This is accomplished by closing movable jaw 18 to position surgical needle 200 within needle receiving recess 26 and rotating toggle wheel 62 so as to again engage surgical needle 200 with upper needle securing blade 158. This releases surgical needle 20 from lower needle securing blade 160 and movable jaw 18. Handles 20 may again be moved to open the jaw structure and reposition surgical needle 200 in a position to again repenetrate tissue section X and heart valve cuff material Y as shown in FIG. 23.

Figure 24:
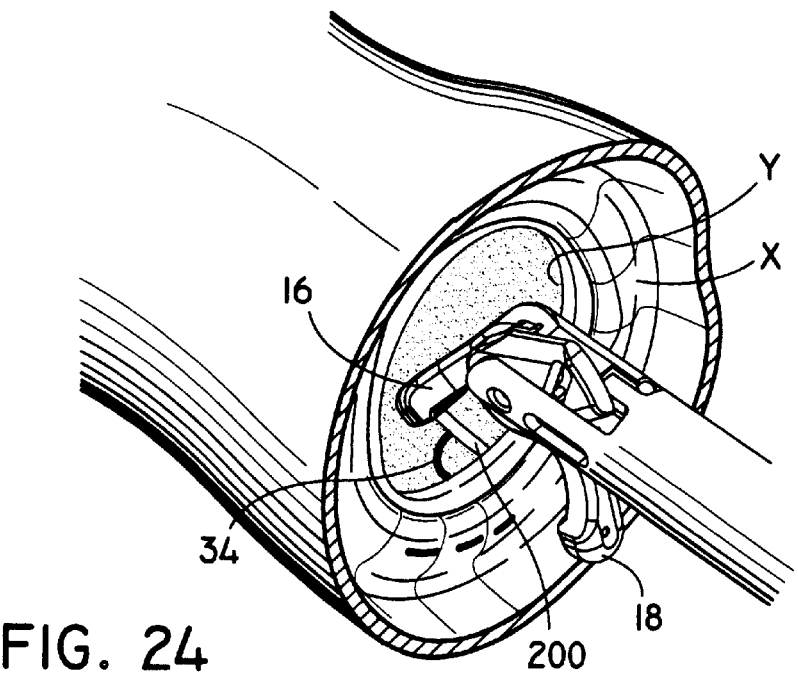
FIG. 24 is a perspective view similar to FIG. 20 after several passings of the surgical needle through the heart valve cuff structure and heart tissue.

As shown in FIG. 24, heart valve cuff material Y may be securely sutured to tissue section X by repeatedly penetrating X and Y with elongated penetrating portion 204 of surgical needle 200 and drawing and wrapping length of suture material 34 about tissue section X and heart valve cuff material Y. Alternatively, surgical suturing apparatus 10 may be used to only install stitches in heart tissue X alone and an accessory needle may be used to pass the ends of the sutures through heart valve cuff material Y in the manner described hereinbelow.

Figure 25:
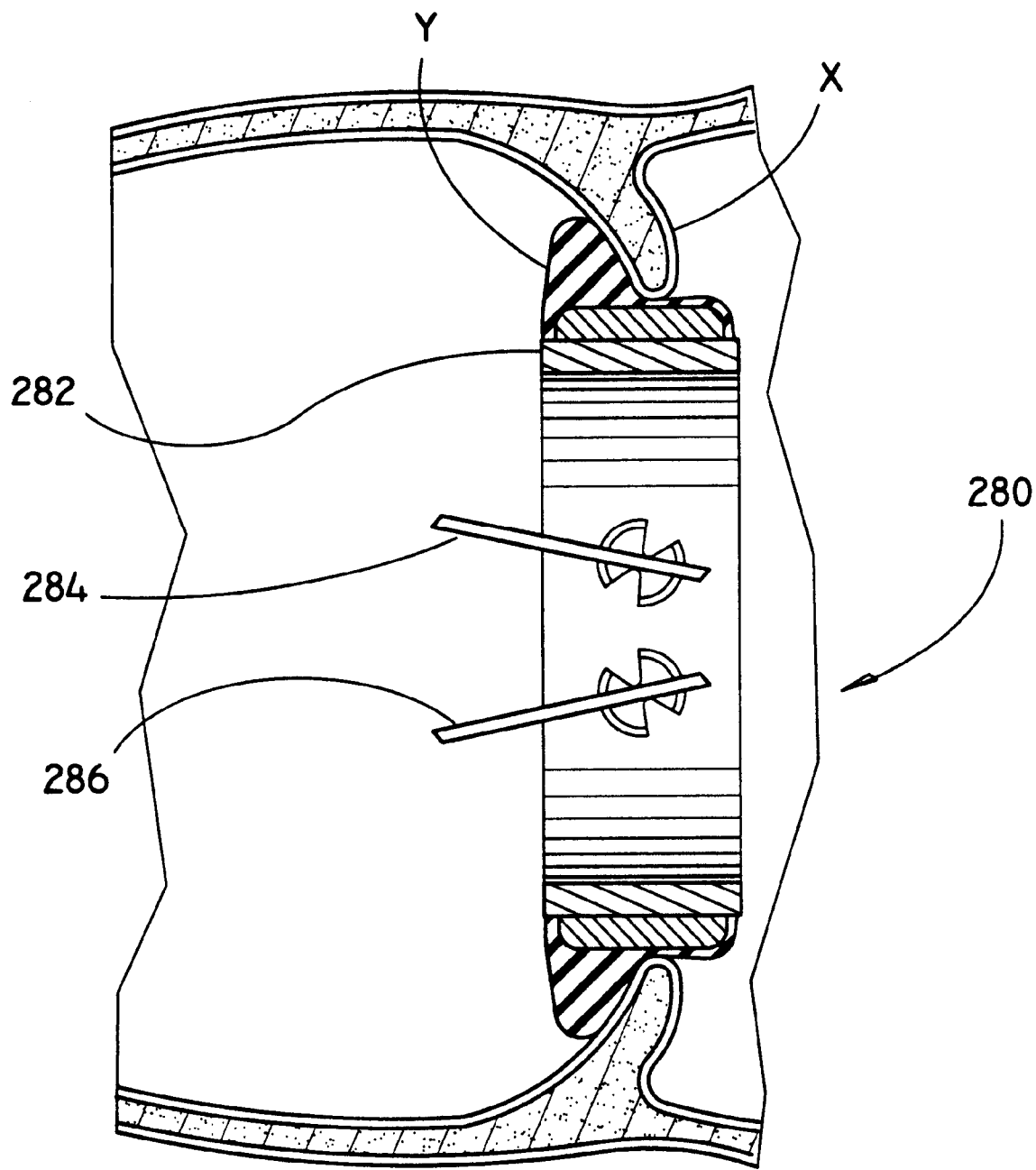
FIG. 25 is a sectional view of a replacement heart valve and valve cuff positioned within heart tissue.

Referring to FIG. 25, there is shown a replacement heart valve 280 associated with heart valve cuff material Y. As noted above, the structure of heart valve 280 was previously affixed to heart valve cuff material Y before cuff material Y is sutured to tissue section Y. Heart valve 280 generally includes a heart valve ring 282 having a pair of heart valve leaflets 284 and 286 pivotally mounted thereon.

Figure 26:
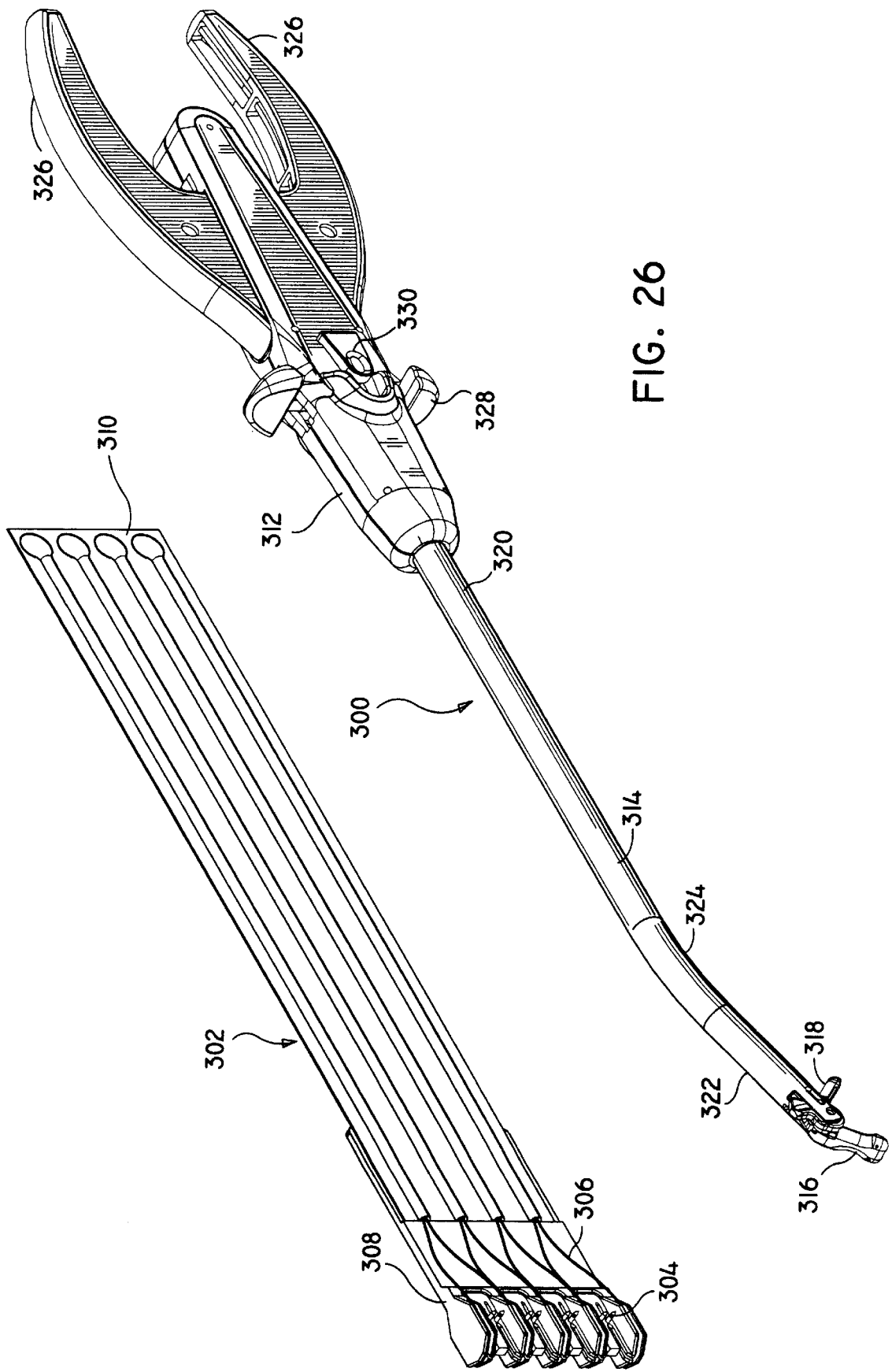
FIG. 26 is a perspective view of a dual needle stitching device and a disposable loading unit for use in heart valve replacement surgery.

Referring now to FIG. 26, there is illustrated a novel dual needle stitching device 300 and a disposable loading unit 302 for providing surgical incision members 304 and associated lengths of suture material 308 for use in stitching device 300. Disposable loading unit 302 generally includes an incision member support 308 configured to releasably retain a plurality of opposed pairs of surgical needles or surgical incision members 304 in a manner described hereinbelow. Disposable loading unit 302 also includes a suture support 310 affixed to incision member support 308 and configured to releasably retain lengths of suture material 306 associated with the surgical incision member pairs in a manner also described hereinbelow.

Dual needle stitching device 300 generally includes a handle housing 312 and an elongated tubular housing or body portion 314 extending distally from handle housing 312. A pair of incision member or needle receiving jaws including a first or stationary jaw 316 and a second or movable jaw 318 are mounted on a distal end of body portion 314. Each of movable jaw 318 and stationary jaw 316 are configured to receive a pair of surgical needles or incision members 304. Body portion 314 includes a first linear portion 320, a second linear portion 322 and an arcuate portion 324 intermediate first and second linear portions 320 and 322. Second linear portion 322 illustratively forms an angle of approximately 20° relative to first linear portion 320 by means of angled portion 324. Other angles are also contemplated. The 20° angle or offset of second linear portion 322 relative to first linear portion 320 facilitates use of stitching device 300 during heart valve replacement surgery. Preferably, stationary jaw 316 is mounted at a predetermined angle of approximately 60° relative to the longitudinal axis of second linear portion 322 although other angles can also be utilized.

Handle housing 312 is substantially structurally and functionally identical to handle housing 12 described hereinabove with regard to surgical suturing apparatus 10. Handle housing 312 generally includes a pair of handles 326 movably mounted to handle housing 312 to control the movement of movable jaw 318 relative to stationary jaw 316. Preferably, movable jaw 318 moves through an arc of approximately 30° relative to stationary jaw 316. It should be appreciated that, alternatively, both jaws could be movable.

Stitching device 300 further includes a securing mechanism 328 to releasably and alternately secure a pair of surgical incision members 304 within stationary jaw 316 and movable jaw 318. A loading mechanism 330 is provided to override securing mechanism 328 and allow the pair of surgical incision members to be loaded simultaneously. Loading mechanism 330 is substantially structurally and functionally identical to loading mechanism 24 described above with respect to apparatus 10.

Figure 27:
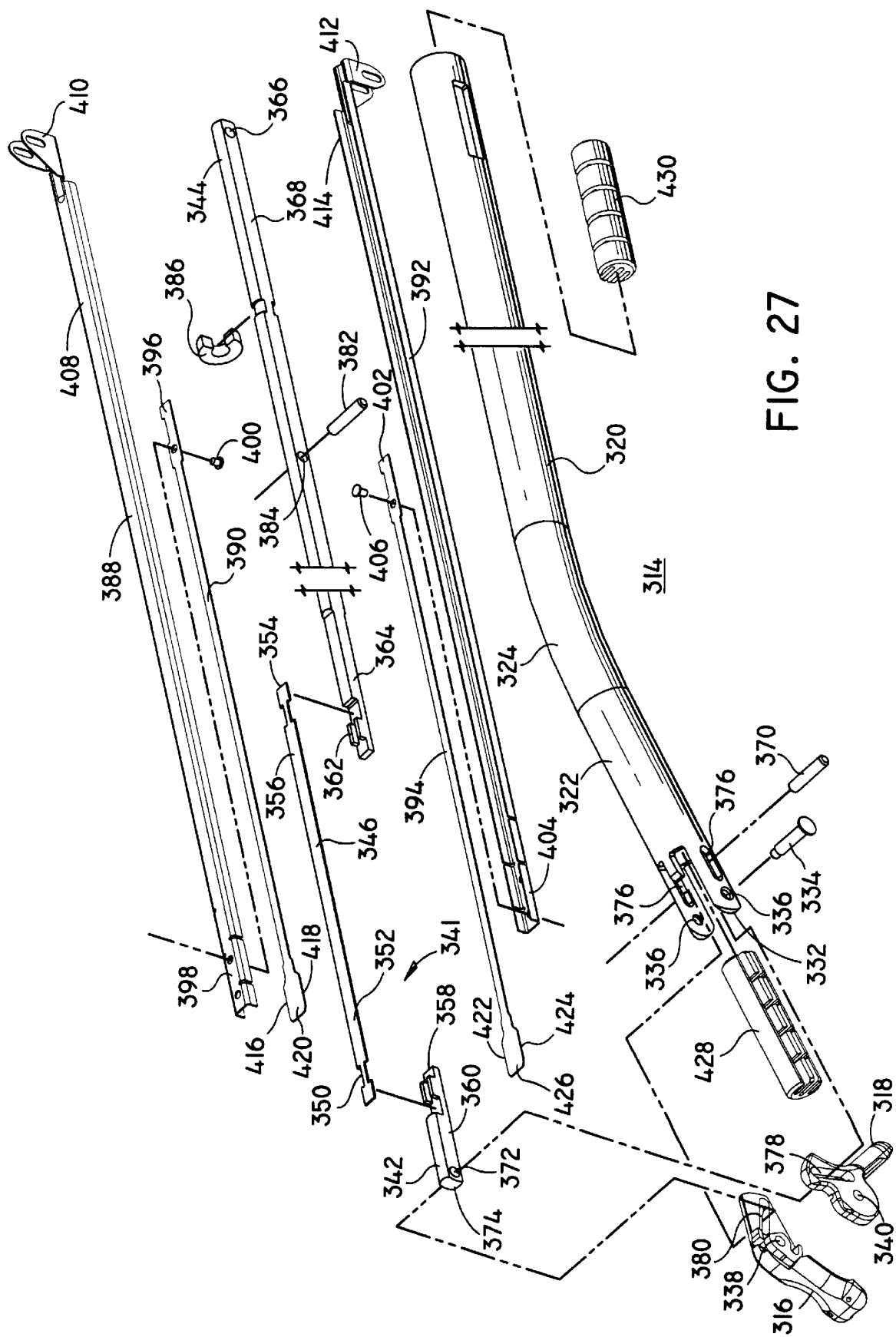
FIG. 27 is a perspective view, with parts separated, of a distal end portion of the dual needle stitching device of FIG. 26.

Referring now to FIG. 27, stationary jaw 316 and movable jaw 318 are mounted to a distal end 332 of second linear portion 322 by means of a pin 334. Pin 334 extends through holes 336 on second linear portion 322 and through holes 338, 340 formed in stationary jaw 316 and movable jaw 318, respectively. Movable jaw 318 is free to rotate about pin 334. As described below, stationary jaw 316 may also rotate about pin 334.

Similar to that described hereinabove with regard to surgical suturing apparatus 10, movable jaw 318 is movable toward and away from stationary jaw 316 in response to actuation of handles 326 (FIG. 26). However, since body portion 314 includes an arcuate portion 324, body portion 314 is provided with a composite center rod 341 having a relatively rigid distal center rod section 342, a relatively rigid proximal center rod section 344 and a relatively flexible central section 346 intermediate proximal and distal center rod sections 342, 344, respectively. Central section 346 has a first male fitting 350 at a distal end 352 and a second male fitting 354 at a proximal end 356 thereof. Central section 346 is connected to distal center rod section 342 by engagement of first male fitting 350 with a female fitting 358 formed in a proximal end 360 of distal center rod section 342. Similarly, central section 346 is affixed to proximal center rod section 344 by engagement of second male fitting 354 with a female fitting 362 formed on a distal end 364 of proximal center rod section 344.

Proximal center rod section includes a hole 366 at a proximal end 368 thereof to receive a pin associated with a linkage (not shown) similar to that described hereinabove with respect to apparatus 10 and connect proximal center rod section to handles 326. In order to open and close movable jaw 318 in response to longitudinal motion of distal center rod section 342, distal center rod section 342 is provided with a camming pin 370 positioned within a hole 372 in a distal end 374 of distal center rod section 342. Camming pin 370 extends into and is guided by slots 376 formed in distal end 332 of second linear portion 322. Camming pin 370 moves within an angled slot 378 in movable jaw 318 to cam movable jaw 318 between open and closed positions in response to actuation of handles 326. Camming pin 370 also moves within a longitudinal slot 380 formed within stationary jaw 316. Slot 380 is aligned with slots 376 in second linear portion 322 and thus camming pin 370 imparts no motion to stationary jaw 316. However, it will be appreciated that stationary jaw 316 can easily be, and preferably is, made movable by forming slot 380 at an angle in a manner similar to that of angled slot 378 in movable jaw 318 and as described above with respect to surgical suturing apparatus 10.

Longitudinal movement of proximal center rod section 344 moves distal center rod section 342 longitudinally to open and close movable jaw 318 relative to stationary jaw 316 in response to actuation of handles 326.

Proximal center rod section 344 is provided with a pin 382 extending through a hole 384 and which blocks the securing mechanism, in particular, a toggle wheel, from moving when distal center rod section 342 is in a distal position, corresponding to an open jaw condition in a manner identical to that described hereinabove with respect to surgical suturing apparatus 10. Proximal center rod section 344 also provided with a C-ring 386 which provides an abutment surface for a handle biasing spring (not shown).

As noted above, stitching device 300 is provided with a securing mechanism which releasably and alternately secures a pair of surgical incision members within stationary jaws 316 and movable jaw 318. The securing mechanism of stitching device 300 functions substantially similar to that associated with surgical suturing apparatus 10 and, in general, includes in part an upper channel member 388 having an upper needle securing blade 390 extending distally therefrom and a lower channel member 392 having a lower needle securing blade 394 extending therefrom. A proximal end 396 of upper needle securing blade 390 is affixed to a distal end 398 of upper channel member 388 by means of a pin 400. Similarly, a proximal end 402 of lower needle securing blade 394 is affixed to a distal end 404 of lower channel member 392 by means of a pin 406. A proximal end 408 of upper channel member 388 is provided with mounting structures 410 configured to engage and function with a toggle wheel (not shown) in substantially the same manner as that described with respect to surgical suturing apparatus 10. Similarly, lower channel member also includes mounting structure 412 at a proximal end 414 thereof for engagement with the toggle wheel.

As noted above, stitching device 300 alternately and releasably secures a pair of surgical incision members within stationary jaw 316 and movable jaw 316. Upper needle securing blade 390 includes opposed needle engaging surfaces 416, 418 on an enlarged distal blade surface 420. Each of surfaces 416, 418 engage a notch formed in a surgical incision member positioned within stationary jaw 316 when upper needle securing blade 390 is advanced therein in a manner described hereinbelow. Lower needle securing blade 394 also includes an opposed pair of needle engaging surfaces 422, 424 on an enlarged distal blade surface 426 and cooperates with movable jaw 318 to releasably secure a pair of surgical incision members therein.

In order to prevent upper and lower needle securing blades 390 and 394, as well as central section 346, from flexing away from their respective axis or "bowing" within body portion, there are provided a proximal stabilizer member 428 and a distal stabilizer member 430, both of which and substantially identical and which are configured to be inserted within body portion 314.

Figure 28:
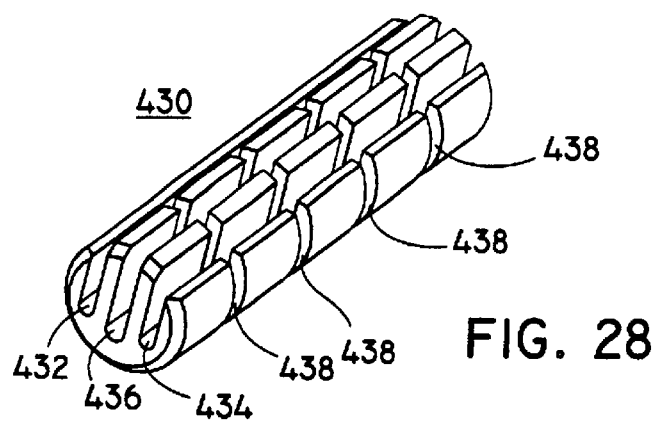
FIG. 28 is a perspective view of a stabilizer provided within the distal end portion of FIG. 27.

Referring now to FIG. 28, distal stabilizer 430 includes an upper blade receiving slot 432, a lower blade receiving slot 434 and a central section receiving slot 436. Distal stabilizer 430 is sectioned at points 438 to allow distal stabilizer 430 to slightly flex and conform to the curvation of arcuate portion 324 of body portion 314 (FIG. 29).

Figure 29:
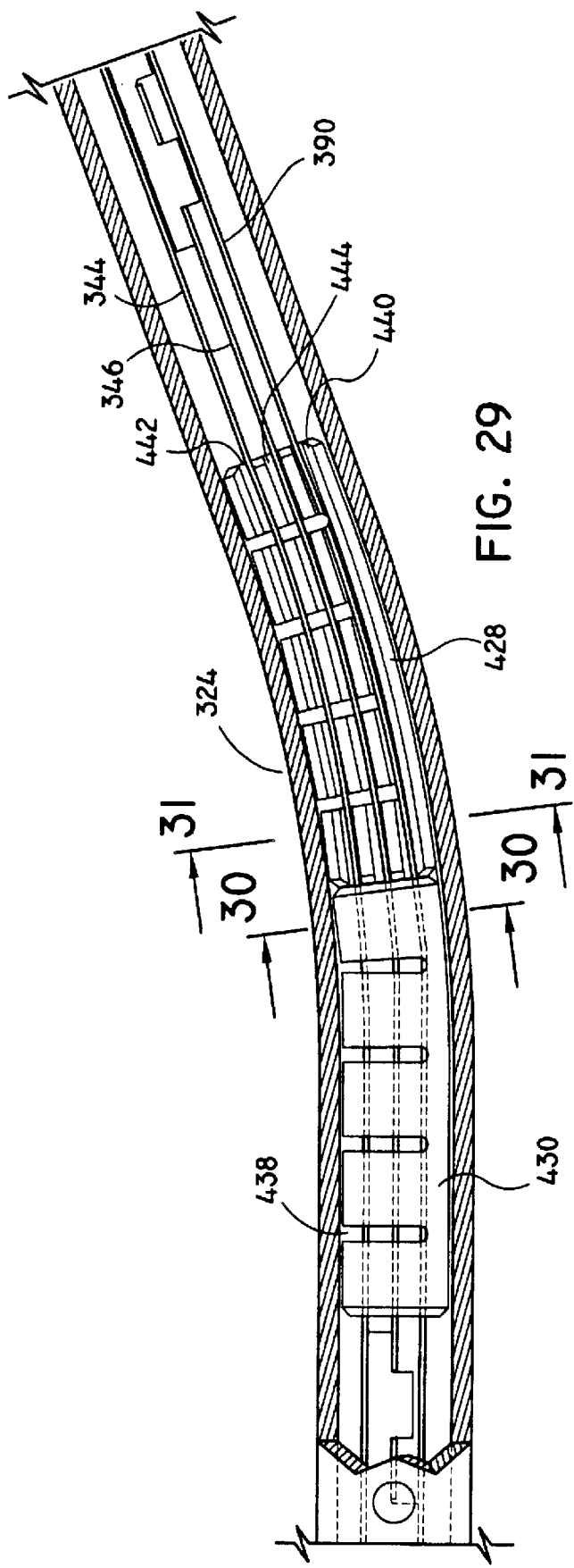
FIG. 29 is a side view, partially shown in section of a portion of the distal end portion of FIG. 27.

As shown in FIG. 29, proximal stabilizer 428, also includes an upper blade receiving slot 440, a lower blade receiving slot 442 and a central section receiving slot 444. Additionally, proximal distal stabilizer 428 is also sectioned on one side at points 446 to facilitate bending within arcuate portion 324 of body portion 314.

Figure 30:
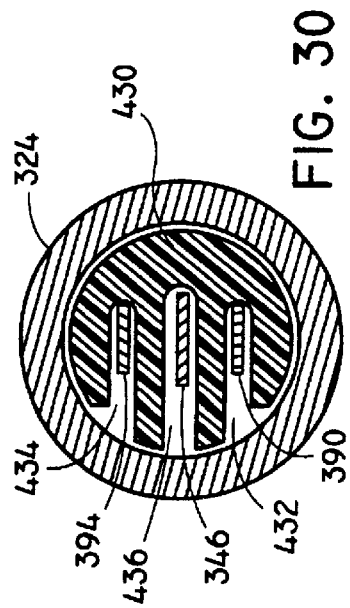
FIG. 30 is a sectional view taken along line 30—30 of FIG. 29.

Referring to FIG. 30, upper needle securing blade 390 is slidingly received within and guided by slot 432 in distal stabilizer 430. Lower needle securing blade 394 is similarly received in slot 434 and central section 346 of the center rod is received within slot 436 of distal stabilizer 430.

Figure 31:
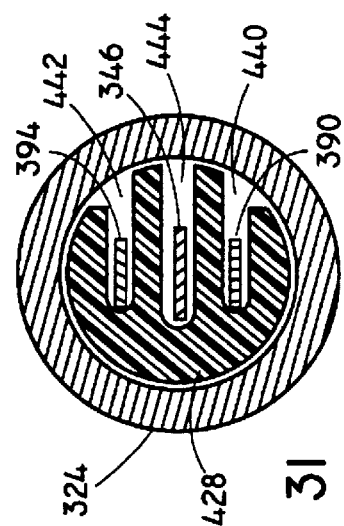
FIG. 31 is a sectional view taken along line 31—31 of FIG. 29.

As shown in FIGS. 29 and 31, upper needle securing blade 390 is similarly received within slot 440 of proximal stabilizer 428, lower needle securing blade 394 is received within slot 442 and central section 346 of the center rod is received within slot 444 of proximal stabilizer 428.

Figure 32:
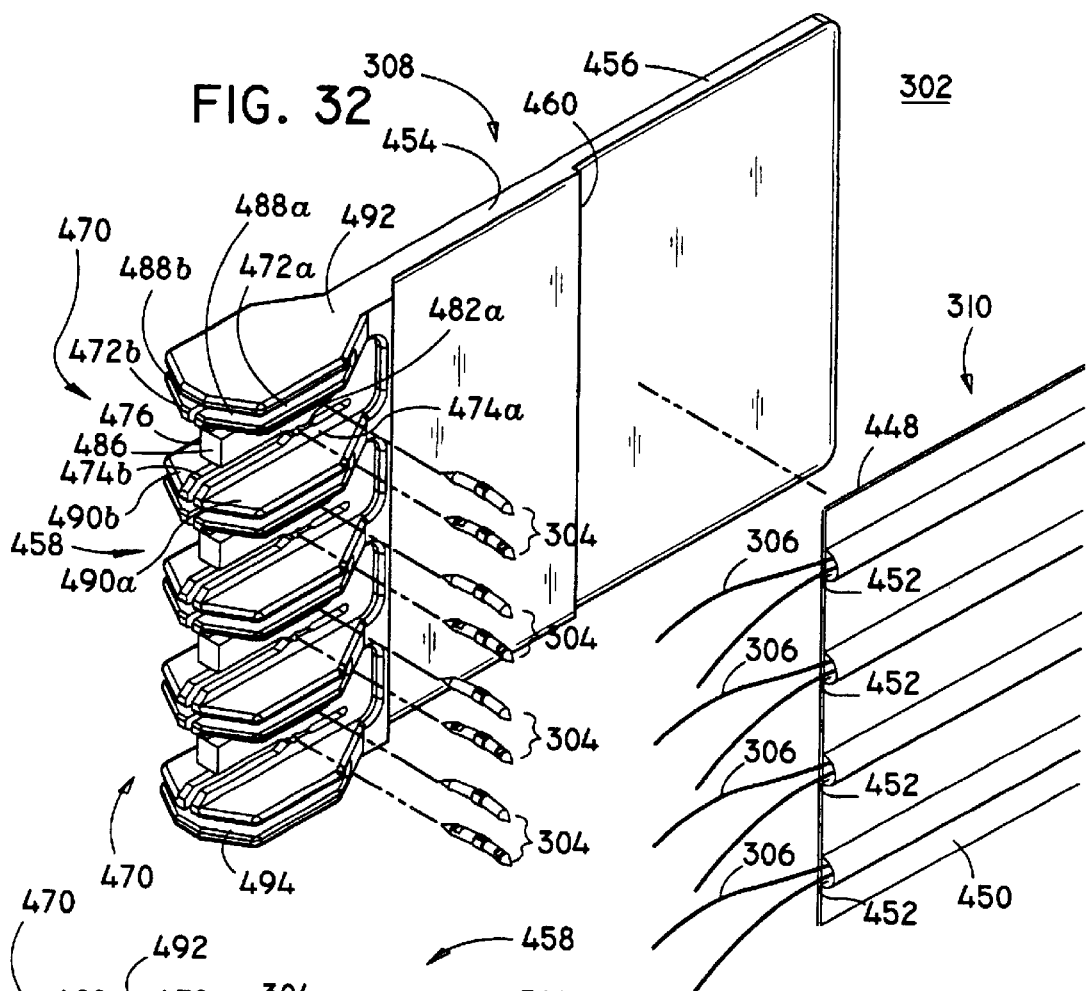
FIG. 32 is a perspective view, with parts separated, of the disposable loading unit of FIG. 26.

Referring now to FIG. 32, the details of disposable loading unit 302 including incision member support 308 and suture support 310 will now be described. Suture support 310 is provided to retain a plurality of lengths of suture, such as, for example, suture material 306, in sterile condition. Suture support 310 generally includes a backing 448 having a cover 450 adhered thereto. Cover 450 is adhered to backing 448 so as to create a plurality of longitudinally extending tubes 452 thereon. Length of suture material 306 are received within tubes 452.

Incision member support 308 generally includes a center portion 454, a distal portion 456, and a proximal portion 458. An abutment edge 460 is formed intermediate center portion 454 and distal portion 456. Abutment edge 460 is provided to allow alignment of suture support 310 in order to affix suture support 310 to distal portion 456. Specifically, a proximal portion of suture support 310 is adhered to distal portion 456 through the use of various adhesives to proximal portion 456.

Figure 33:
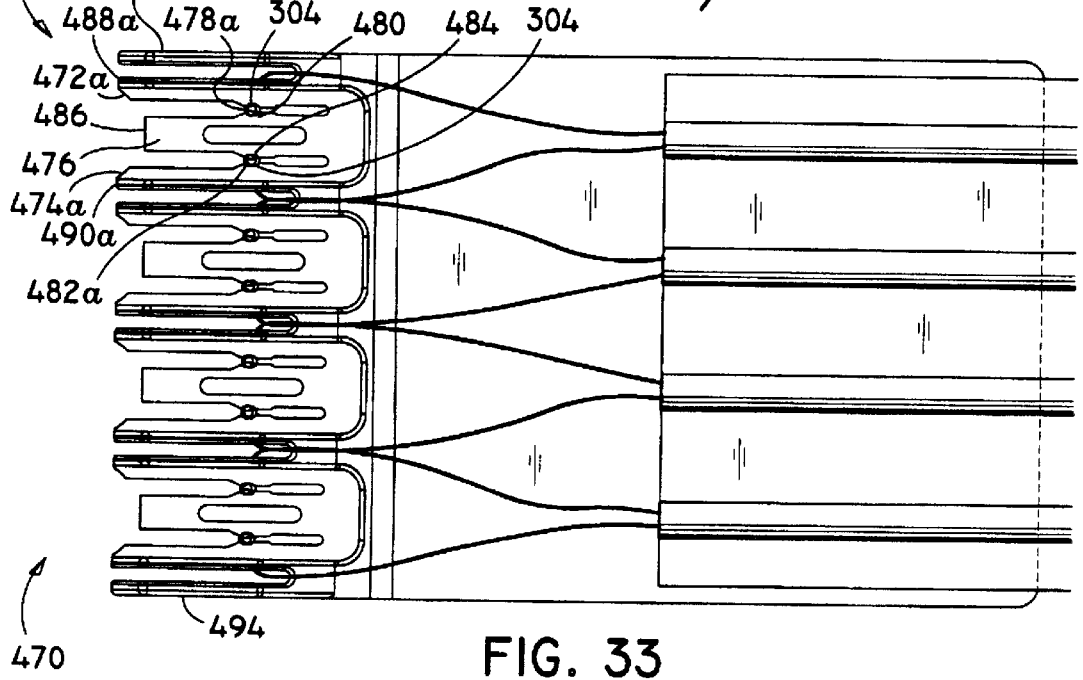
FIG. 33 is a partial top plan view of the disposable loading unit of FIG. 26.

As noted above, disposable loading unit 302 is provided to securely and releasably retain a plurality of pairs of surgical needles or surgical incision members, such as surgical incision member 304, in position to be grasped by dual needle stitching device 300. Referring to FIGS. 32 and 33, proximal portion 458 generally includes a plurality of needle supply stations 470 each of which contains a pair of surgical incision members 304. As shown, each needle supply station generally includes a first flexible arm 472, which may be formed as complementary halves 472a and 472b and a second flexible arm 474 which may also be formed as complementary halves 474a and 474b. A center stud 476 extends intermediate first flexible arm 472 and second flexible arm 474. While multiple needle supply stations 470 are illustrated on disposable loading unit 302, the following description will be directed to a single disposable loading unit. It should be appreciated that any number of needle supply stations 470 may be provided on disposable loading unit 302.

In order to retain pairs of surgical needles 304 between first and second flexible arms 472 and 474, and center stud 476, a first notch 478 is formed on first flexible arm 472. Specifically, each of flexible arms 472a and 472b incorporate a notch 478a and 478b (not shown). Center stud 476 is provided with a corresponding notch 480. It should be noted that when a length of suture 306 is attached centrally within surgical incision member 304, surgical incision member 304 is retained against first stud notch 480 by notches 478a and 478b. Length of suture material 306 is allowed to extend between first and second flexible arms 472a and 472b. Similarly, second flexible arm 474 includes second flexible arm notches 482a and 482b (FIG. 34) which securely retain the second surgical incision member 304 against the second stud notch 484. First and second flexible arms 472 and 474 are sufficiently flexible so as to allow surgical incision member 304 to be free from disposable loading unit 302.

To guide distal end of dual needle stitching device 300 into alignment about surgical incision members 304 retained on disposable loading unit 302, center stud 476 has an abutment end 486 which is configured to limit the advancement of dual needle stitching device 300 between first flexible arm 472 and second flexible arm 474. Additionally, first flexible arm 472 is provided with a pair of jaw guides 488a and 488b and second flexible arm 474 is provided with a pair of second flexible jaw guides 490a and 490b. While abutment end 486 limits advancement of dual needle stitching device 300 within needle supply stations 470, first and second jaw guides 488 and 490 serve to guide stationary jaw 316 and movable jaw 318 about surgical incision members 304. In order to prevent inadvertent flexing of flexible arms at needle supply stations adjacent ends of disposable loading unit 302, disposable loading unit 302 is provided with a pair of relatively rigid side guards 492 and 494 which protect needle supply stations 470.

Figure 34:
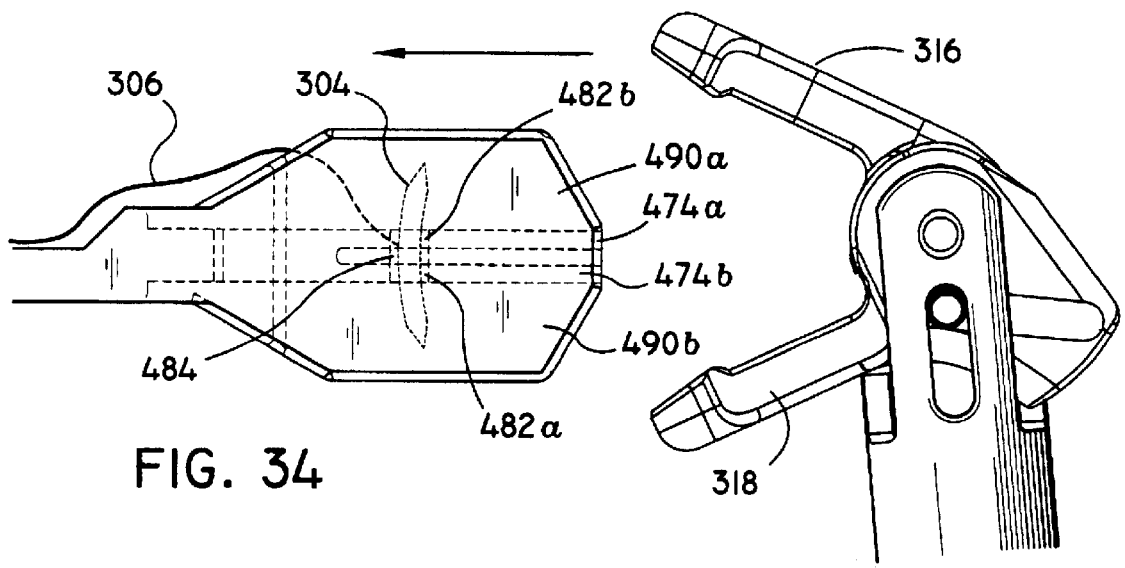
FIG. 34 is a side view of the jaw structure of the stitching device of FIG. 26 being advanced toward a needle carrying end of the disposable loading unit of FIG. 26.

Referring now to FIGS. 34–38, the use of loading unit 302 to supply a pair of surgical incision members 304 connected by a single length of suture material 306 will now be described. Referring initially to FIG. 34 the distal end of stitching device 300 with movable jaw 318 in an open condition spaced apart from stationary jaw 316 is advanced toward one of the needle supply stations of disposable loading unit 302. In particular, movable jaw 318 and stationary jaw 316 are advanced toward needle supply station such that jaws 316 and 318 pass between and are guided by first jaw guides 488a and 488b (not shown) and second jaw guides 490a and 490b. As noted above, a surgical incision member is releasably retained between second notches 482a and 482b on second flexible arms 474a and 474b and notch 480 on center stud 476.

Figure 35:
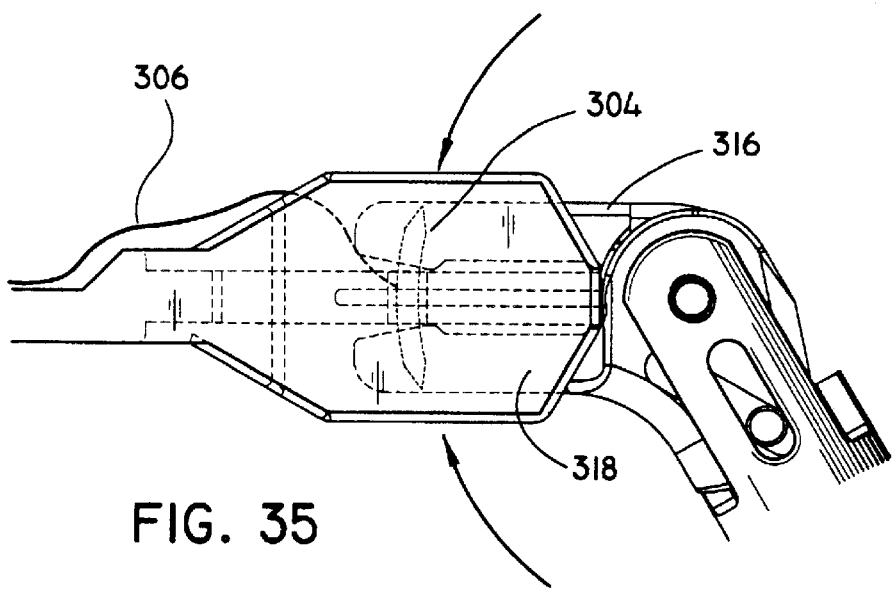
FIG. 35 is a view similar to FIG. 34 and illustrating the jaw structure being closed about a suturing needle held on the disposable loading unit.

Referring now to FIG. 35, as handles 326 (FIG. 1) are moved to a closed position movable jaw 318 is moved toward stationary jaw 316 to close about surgical incision member 304.

Figure 36:
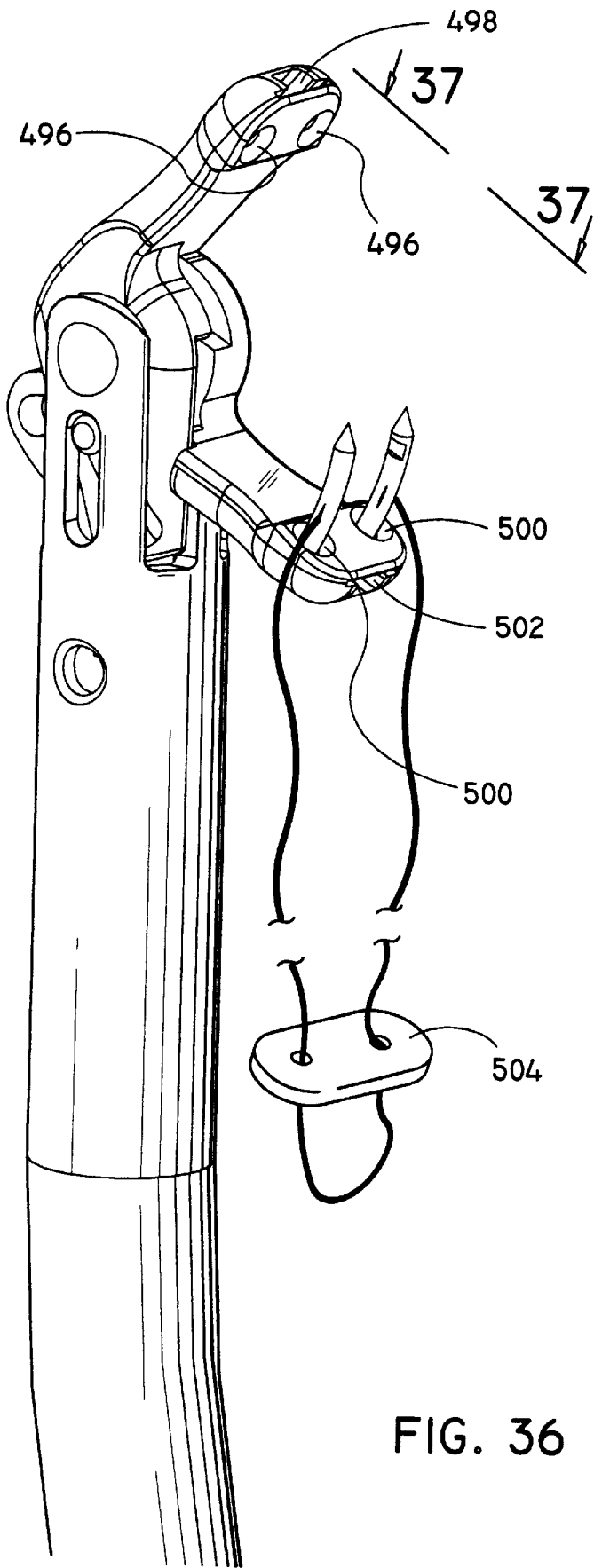
FIG. 36 is a perspective view of the distal end of the stitching device of FIG. 26 with a double needle suture, having a pledget, installed in the jaw structure thereof.

Referring to FIG. 36, stationary jaw 316 is provided with a pair of recesses 496 for receipt of the pair of incision members 304 held within a needle supply station. Stationary jaw 316 also includes a slot 498 which slidingly receives enlarged distal blade surface 420 of upper needle securing blade 390 (FIG. 27). Slot 498 intersects recesses 496. Similarly, movable jaw 318 includes a pair of recesses 500 for receipt of a pair of incision members 304 and a slot 502 for receipt of enlarged distal blade surface 426 of lower needle securing blade 394 (FIG. 27). As shown, preferably, a pledget 504 is provided on suture 306 to serve as a backing or anchor when a stitch is applied to heart tissue. An example of a pledget 504 is described in copending patent application entitled "SURGICAL SUTURING DEVICE" filed on even date herewith under Express Mail Label No. IB701310731US, the entire disclosure of which is incorporated by reference herein.

Referring to FIGS. 37 and 38, when lower needle securing blade 394 is moved to a distalmost position needle engaging surfaces 422 and 424 of enlarged distal blade surface 426 intersect recesses 500. As shown in FIG. 38, needle engaging surfaces 422 and 424 engage first blade engaging notches 506 formed in incision members 304 to secure incision members within movable jaw 318. Incision members 304 also include second blade engaging notches 508 to receive needle engaging surfaces 416 and 418 of upper needle securing member 390 in order to secure incision members 304 within stationary jaw 316.

Figure 40:
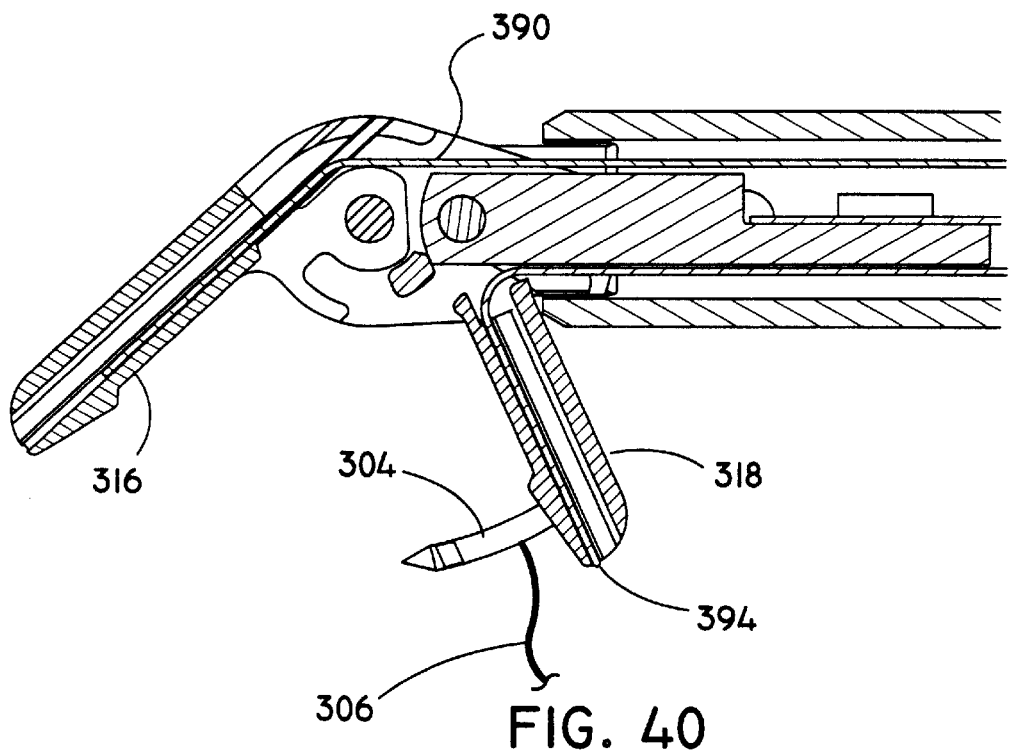
FIG. 40 is a side sectional view illustrating a surgical needle installed in the movable jaw.
Figure 41:
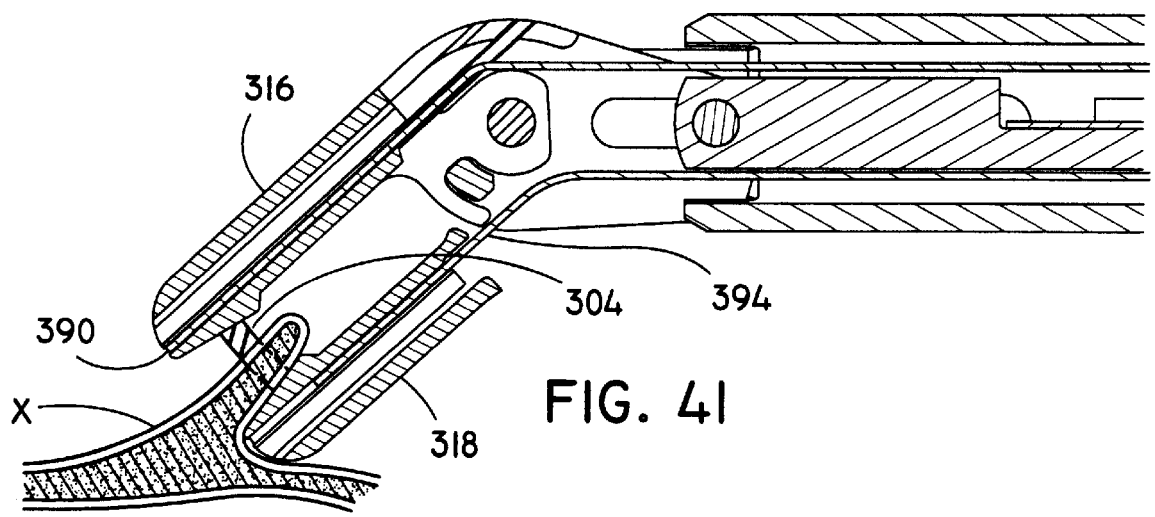
FIG. 41 is a side sectional view illustrating closing of the movable jaw toward a stationary jaw to pierce the heart tissue.
Figure 42:
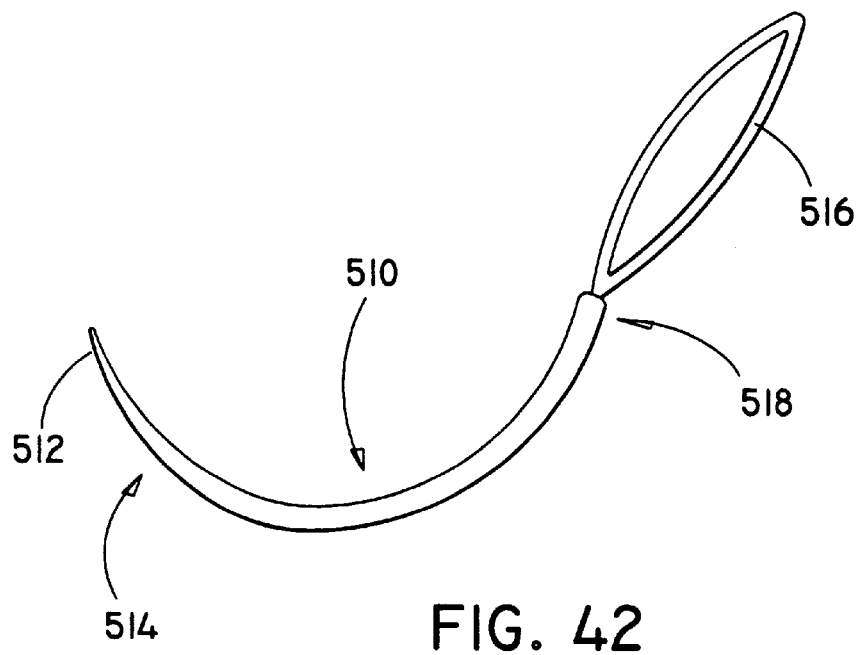
FIG. 42 is a perspective view of a surgical needle used to suture the heart valve cuff to the heart tissue.

Referring now to FIGS. 39 to 41, the use of stitching device 300 to form a stitch between a section of heart valve tissue X and a replacement heart valve will now be described. It will be appreciated that while only a replacement heart valve cuff Y is illustrated, the stitching procedure is carried out with a complete replacement heart valve such as that illustrated in FIG. 25 above. Initially, with reference to FIG. 39, stationary jaw 316 is positioned on one side of tissue X and movable jaw 318 retaining incision members 304 is positioned on an opposite side. As shown in FIG. 40 incision members 304 are retained within movable jaw 318 by engagement with lower needle securing member 394 while upper needle securing member 390 is in a proximalmost position within stationary jaw 316.

Stitching device 300 is actuated, by closing handles 326 (FIG. 1), to move stationary jaw 318 and incision members to a closed position adjacent stationary jaw 316 thereby causing incision members 304 to pierce heart tissue X as shown in FIG. 41. As shown, lower needle securing member 394 has been retracted to a proximalmost position to release incision members 304 from movable jaw 318 and upper needle securing member 390 has simultaneously been advanced to a distalmost position to securely grasp incision members 304 within stationary jaw 316. Thus upon opening jaws 316 and 318 the pair of incision members 304 can be drawn through tissue X thereby drawing length of suture material 306 therethrough until pledget 504 contacts tissue X (FIG. 43A). Stitching device 300 is reloaded as described above and the procedures are repeated to form a plurality of stitches as shown.

In order to stitch together the circumference of tissue X and valve cuff Y, there may be provided a suturing needle of the type described in an application entitled "SUTURE NEEDLE AND METHOD" and filed on even date herewith under Express Mail Label No. IB701310720US, the entire disclosure of which is incorporated by reference herein. Needle 510 preferable has a tissue penetrating point 512 at a distal end 514 thereof and a suture retaining loop 516 extending from a proximal end 518 thereof. As shown in FIG. 43A,in order to stitch cuff Y to tissue X, incision members 304 are removed from suture material 306 and a first free end 520 of suture material 306 is threaded through loop 516, Needle 510 can now be used to form more stitch through tissue X and valve cuff Y. Needle 510 may be used to repeat the process with the other free end 522 of suture material 306.

Figure 43:
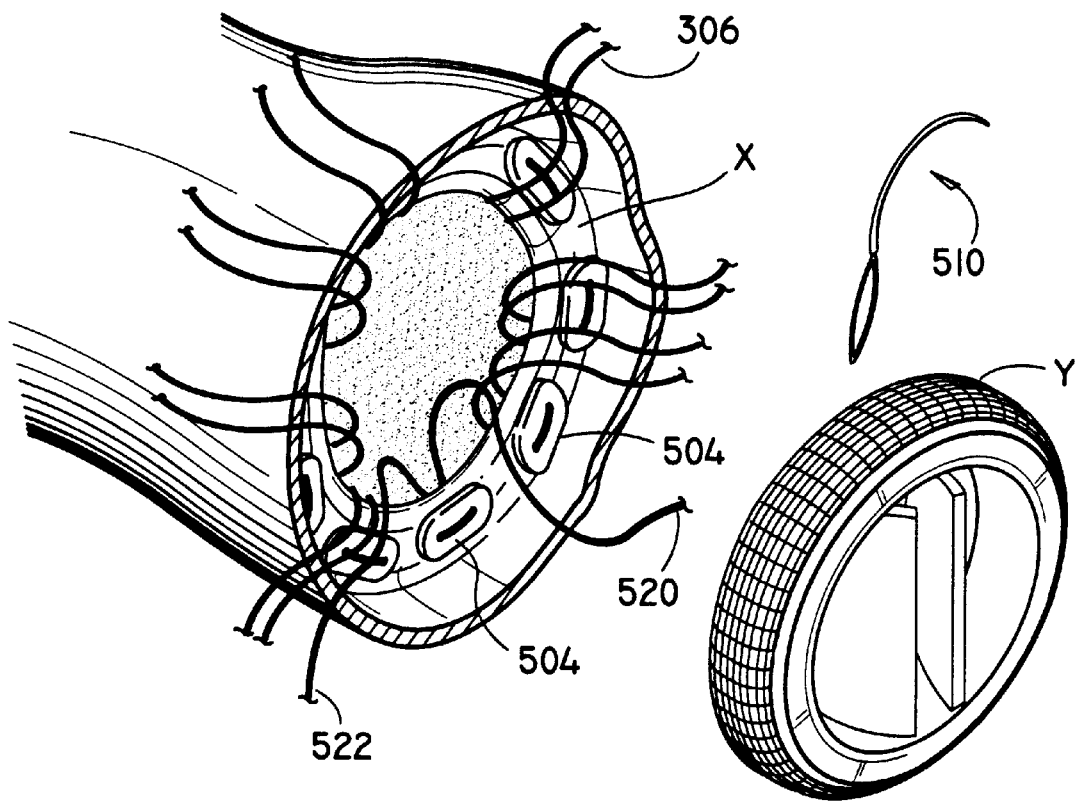
FIG. 43 is a perspective view of the heart tissue with multiple suture-pledget assemblies installed therein and in position to be passed through the cuff of an artificial heart valve using the surgical needle of FIG. 42.
Figure 43A:
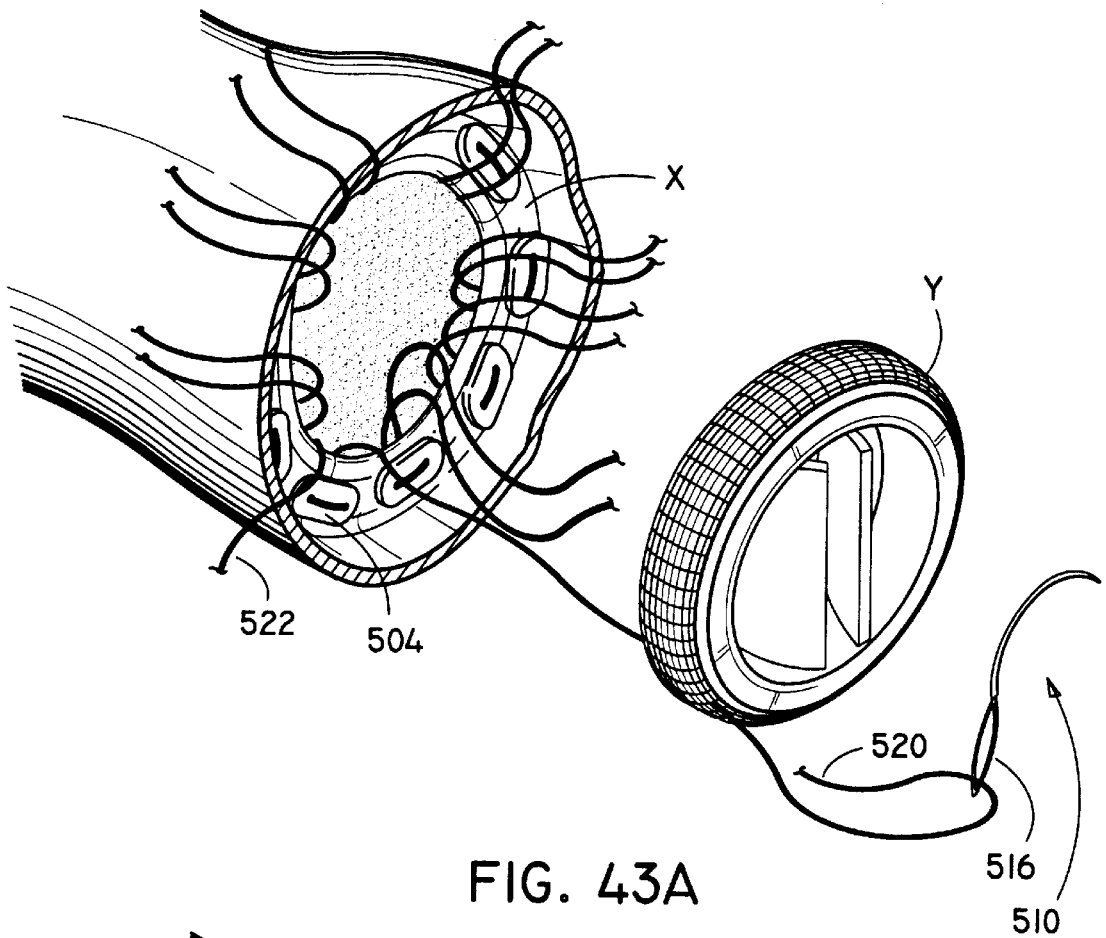
FIG. 43A is a perspective view similar to FIG. 43 and illustrating the use of the surgical needle to pass an end of the suture through the cuff.
Figure 43B:
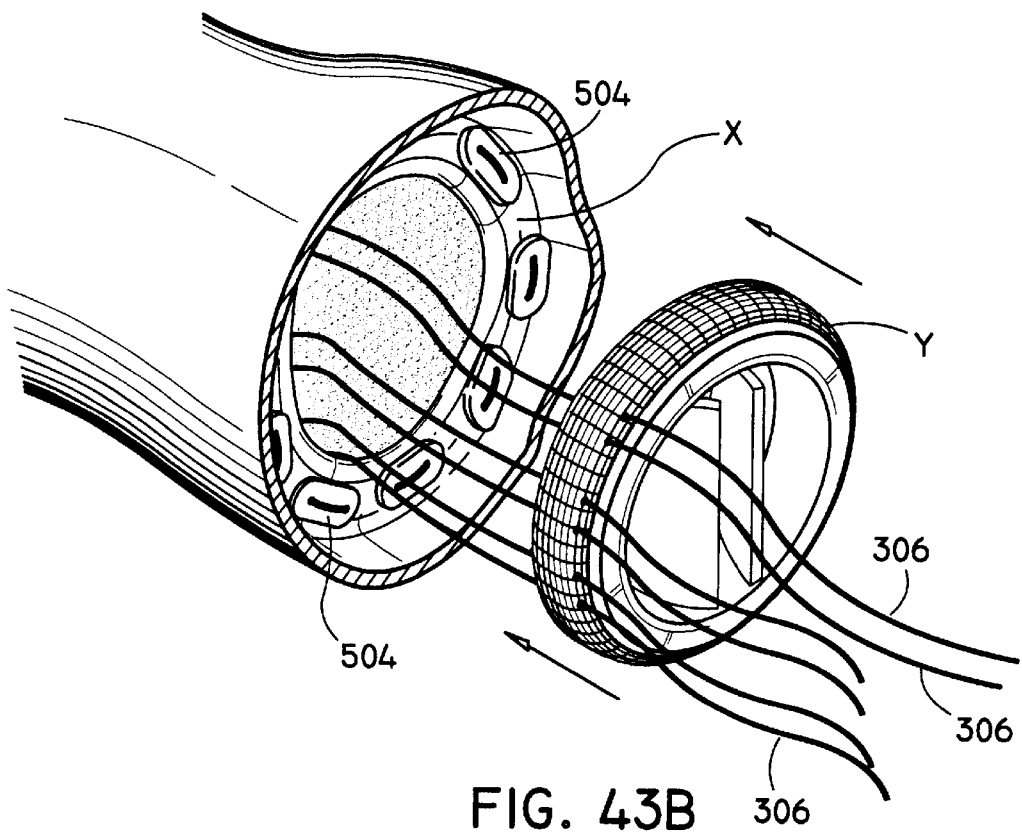
FIG. 43B is a perspective view similar to FIG. 43A with all of the suture ends passed through the cuff and the artificial heart valve being moved down the suture toward heart tissue.

Referring now to FIG. 43B, once all the free ends 520, 522 of suture material 304 have been passed through cuff Y of the artificial heart valve, the sutures may be drawn tight and the artificial heart valve moved or "parachuted" down into place within the heart tissue X. The sutures may then be tied together, preferably in pairs, to affix the artificial heart valve to tissue X.

Figure 43C:
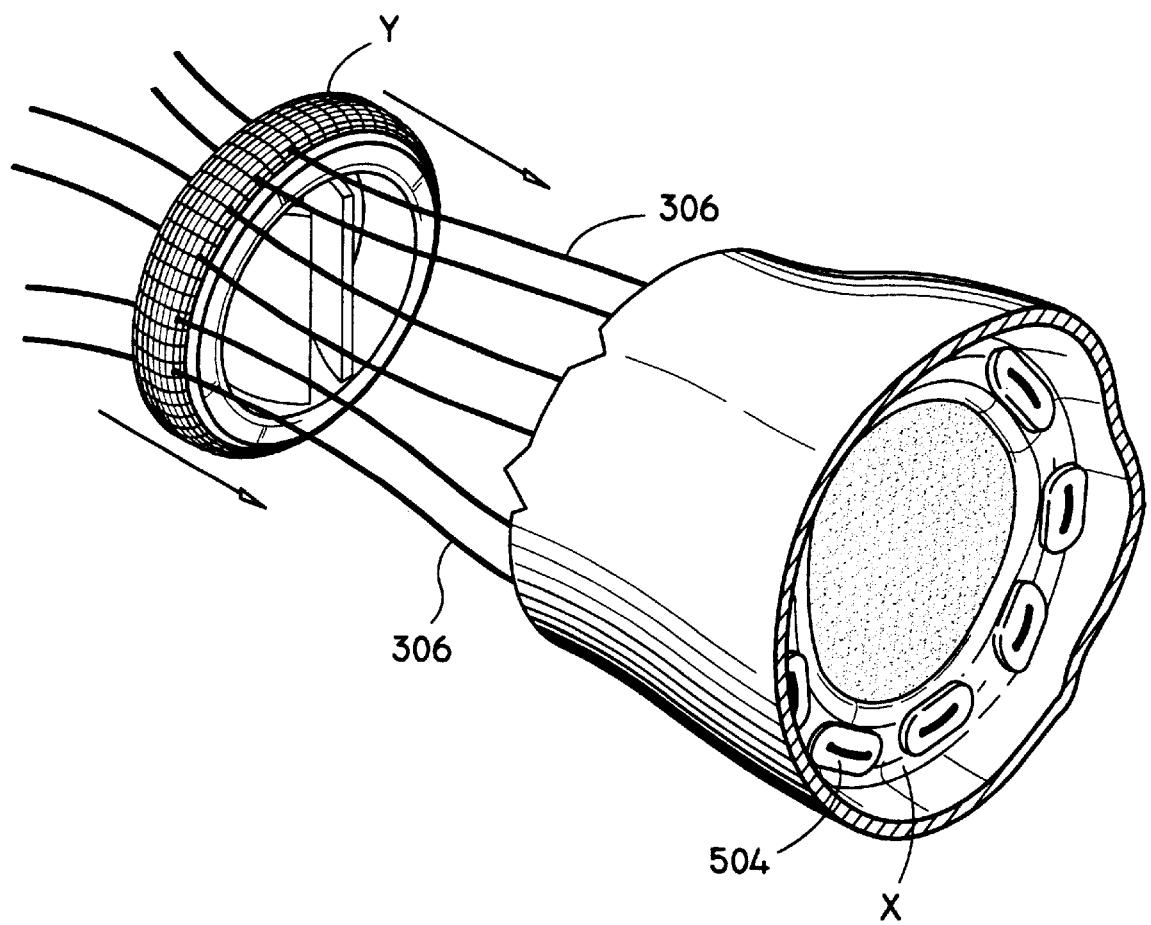
FIG. 43C is a perspective view of an alternate method of suturing the heart valve tissue.

While FIGS. 43–43B show the heart valve approaching the side of the heart tissue adjacent the pledget 504, it is preferable to approach the heart tissue from the opposite side of the heart tissue, i.e., the side with the suture free ends as shown in FIG. 43C.

Figure 44:
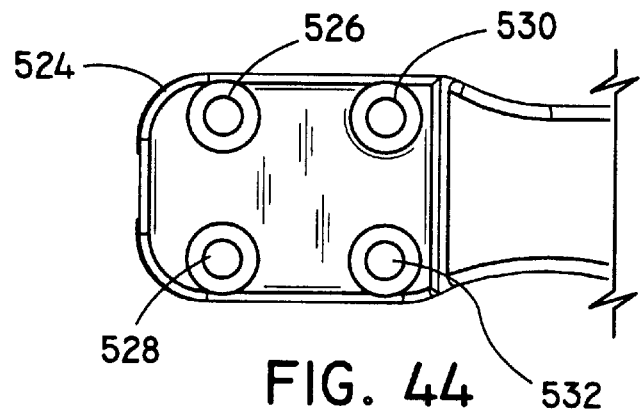
FIG. 44 is a partial view of an alternate jaw structure.
Figure 45:
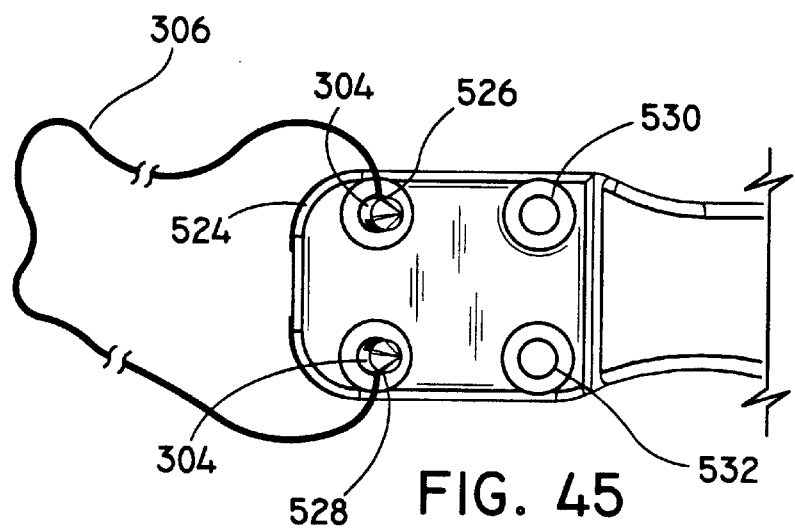
FIG. 45 is a view similar to FIG. 44 illustrating a pair of surgical needles and associated suture installed thereon in a first configuration.
Figure 46:
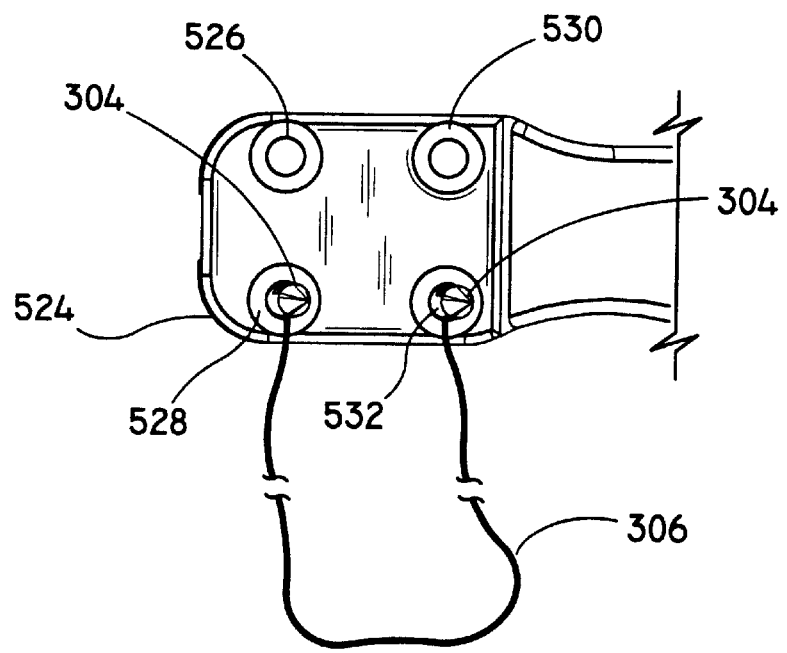
FIG. 46 is a view similar to FIG. 45 with the surgical needle installed in a second configuration.

Referring to FIGS. 44–46 and initially to FIG. 44, an alternate jaw structure 524 is illustrated. Jaw structure 524 includes a pair of distal needle receiving recesses 526, 528 and a pair of proximal needle receiving recesses 530, 532. Dual incision members 304 and associated length of suture material 306 can be retained in various configurations within the recesses as shown. Jaw structure 524 also includes a slot 534 which intersects all four recesses and which slidingly receives a needle securing blade (not shown) to releasably secure incision members or surgical needles within the recesses.

Alternatively, two parallel slots may be provided within jaw structure 524. One of the slots would intersect recesses 526 and 530 on one side of jaw structure 524 while the other slot would intersect recesses 528 and 532 on the other side of jaw structure 524.

As shown in FIG. 45, dual incision members 304 can be positioned in recesses 526 and 528 at the distal end of alternate jaw structure 524 to position incision member 304 as distally as possible on the surgical suturing device. This will allow suturing in tight tissue spaces. Also, should two slots be provided as described above, each incision member 304 may be alternately secured and released within their respective recesses 526, 528.

As shown in FIG. 46, when it is desirable to place stitches in tissue with an edge of a jaw structure 524, dual incision members 304 can be placed in recesses 526, 530 or recesses 528, 532 as shown. It should be understood that incision members 304 may also be placed in the proximal recess 530, 532 when necessary to deeply engage and suture a section of tissue with alternate jaw structure 324.

Further, it may be desirable to place the incision member diagonally across from each other in recess 526 and 532 or 528 and 530. When used with a two slot arrangement described above, the incision members could be alternately secured and released. Further, single or multiple incisions may be provided in the recesses.

It will be understood that various modifications may be made to the embodiments disclosed herein. For example, various angle orientations of the jaw structure as well as elongated body portion may be provided depending upon the particular surgical necessity. While the above description is given with regard to heart valve replacement surgery, it is specifically contemplated that the suturing instruments described herein will find use in other surgical procedures. Therefore, the above description should not be construed as limiting, but merely as exemplifications of preferred embodiments. Those skilled in the art will envision other modifications within the scope and spirit of the claims appended hereto.

What is claimed is:

1. A surgical suturing instrument for use in heart valve replacement surgery comprising:

a housing having an elongated body portion extending distally therefrom;

a first jaw mounted on a distal end of the body portion and oriented at a predetermined angle relative to a longitudinal axis of the body portion, the predetermined angle being greater than 0°;

a second jaw, the second jaw movable between a first position adjacent the first jaw and a second position spaced apart from the first jaw;

at least one handle pivotally mounted to the housing, at least the second jaw movable in response to actuation of the handle;

a securing mechanism for alternately engaging and releasing a surgical needle within at least one of the first and second jaws; and the surgical needle having a curved body portion, an elongated penetrating portion extending from one end of the body portion and a pointed portion extending from an opposite end of the body portion, the needle being received in one of the first and second jaws.

2. The surgical suturing instrument as recited in claim 1, wherein the predetermined angle is approximately 60°.

3. The surgical suturing instrument as recited in claim 1, wherein the second jaw moves through an arc of approximately 50° relative to the first jaw in response to actuation of the at least one handle.

4. A dual needle stitching device for use in surgery comprising:

a housing;

a body portion extending distally from the housing;

a first jaw mounted to a distal end of the body portion, the first jaw configured to receive a pair of surgical incision members therein;

a second jaw mounted to the distal end of the housing, the second jaw configured to receive the pair of surgical incision members therein;

at least one handle mounted on the housing, the second jaw movable relative to the first jaw in response to actuation of the at least one handle; and a securing mechanism operable relative to the first jaw and the second jaw, the securing mechanism operable to alternately secure the pair of surgical incision members within the first jaw and the second jaw.

5. The dual needle stitching device as recited in claim 4, wherein the first jaw is oriented at a predetermined angle relative to a longitudinal axis of the body portion, the predetermined angle being greater than 0°.

6. The dual needle stitching device as recited in claim 4, wherein the second jaw moves through an arc approximately 30° relative to the first jaw in response to actuation of the at least one handle.

7. The dual needle stitching device as recited in claim 4, wherein the first and second jaws each define a pair of recesses therein for receipt of the pair of surgical incision members therein.

8. The dual needle stitching device as recited in claim 7, wherein the securing mechanism includes a needle securing blade movable within a slot in one of the first or second jaws, the slot intersecting both recesses in the respective jaw.

9. The dual needle stitching device as recited in claim 4, wherein at least one of the first and second jaws define a plurality of recesses therein for receipt of the pair of surgical incision members.

10. The dual needle stitching device as recited in claim 9, wherein the securing mechanism includes at least one blade movable within at least one of the first and second jaws to intersect a number of the plurality of recesses.

11. The dual needle stitching device as recited in claim 4, wherein the body portion has a curved portion.

12. A disposable loading unit for use with a surgical suturing apparatus having at least one jaw comprising:

a base;

apparatus receiving structure movably mounted on the base, the apparatus receiving structure configured to receive a distal end of a surgical suturing apparatus; and a needle supply station on the base, the needle supply station having a needle support member movably mounted therein, the needle support member releasably holding at least one surgical needle.

13. The disposable loading unit as recited in claim 12, wherein the apparatus receiving structure is pivotally mounted on the base.

14. The disposable loading unit as recited in claim 13, wherein the needle support member is rotatably mounted on the base.

15. The disposable loading unit as recited in claim 12, wherein the needle support member is movable between a first position presenting a first surgical needle to the distal end of the surgical suturing apparatus and a second position presenting a second surgical needle to the distal end of the surgical suturing apparatus.

16. The disposable loading unit as recited in claim 12, wherein the apparatus receiving structure is movable within a first plane, and the needle support member is movable within a second plane substantially perpendicular to the first plane.

17. A disposable loading unit for use with a dual needle stitching device comprising:

a needle support having a plurality of needle supply stations thereon, each needle supply station configured to releasably retain a pair of surgical needles connected by a single length of suture material; and a suture support affixed to the needle support, the suture support having at least one tube for receipt of the length of suture material.

18. The disposable loading unit as recited in claim 17, wherein each needle station of the plurality of needle stations has a center stud and first and second flexible arms adjacent the center stud, a first needle of the pair of surgical needles being retained between the first flexible arm and the stud and a second needle of the pair of surgical needles being retained between the second flexible arm and the stud.

19. A method of suturing an artificial heart valve to heart tissue comprising the steps of:

providing a suturing device having a first and a second jaw, at least one needle connected to a single length of suture material releasably retained within one of the first and second jaws;

providing an artificial heart valve having a cuff portion;

positioning the at least one needle adjacent heart tissue and the cuff portion of the valve;

closing the jaws to pierce the tissue and cuff portion with the at least one needle;

releasing the at least one needle from the one of the first and second jaws and grasping the at least one needle with the other of the first and second jaws; and opening the first and second jaws to draw the length of suture material through the tissue and cuff portion.

\* \* \* \* \*